United States Patent
Ritvanen et al.

(10) Patent No.: US 12,121,270 B2
(45) Date of Patent: Oct. 22, 2024

(54) IMPLANTABLE OSTEODISTRACTION DEVICE

(71) Applicant: GLOBUS MEDICAL, INC., Audubon, PA (US)

(72) Inventors: Antti Ritvanen, Helsinki (FI); Juha Haaja, Espoo (FI); Harri Hallila, Helsinki (FI); Taneli Kari, Espoo (FI)

(73) Assignee: Globus Medical, Inc., Audubon, PA (US)

( * ) Notice: Subject to any disclaimer, the term of this patent is extended or adjusted under 35 U.S.C. 154(b) by 231 days.

(21) Appl. No.: 17/652,513

(22) Filed: Feb. 25, 2022

(65) Prior Publication Data
US 2023/0270478 A1 Aug. 31, 2023

(51) Int. Cl.
*A61B 17/72* (2006.01)
*A61B 17/00* (2006.01)

(52) U.S. Cl.
CPC ............ *A61B 17/7216* (2013.01); *A61B 2017/00221* (2013.01); *A61B 2017/00411* (2013.01); *A61B 2017/00867* (2013.01)

(58) Field of Classification Search
CPC .............. A61B 17/7216; A61B 17/7225
See application file for complete search history.

(56) References Cited

U.S. PATENT DOCUMENTS

| 5,415,660 A | 5/1995 | Campbell et al. |
| 2005/0010233 A1 | 1/2005 | Wittenstein |
| 2007/0267281 A1* | 11/2007 | Smith ............... A61B 17/068 200/61.53 |
| 2009/0076597 A1* | 3/2009 | Dahlgren ............ A61F 2/2445 606/53 |
| 2009/0173351 A1 | 7/2009 | Sahin et al. |
| 2011/0004246 A1* | 1/2011 | Haaja ............... A61B 17/7216 606/246 |
| 2014/0005788 A1* | 1/2014 | Haaja ................... A61F 2/30 623/18.11 |
| 2015/0369223 A1* | 12/2015 | Hallila .................. F03G 1/10 60/527 |
| 2017/0172624 A1* | 6/2017 | Brunner ............ A61B 17/7225 |

FOREIGN PATENT DOCUMENTS

| DE | 102007036359 A1 | 2/2009 |
| JP | 2013-526952 A | 6/2013 |

(Continued)

*Primary Examiner* — Julianna N Harvey

(57) ABSTRACT

An implantable osteodistraction device includes an inductive power transfer circuit at least partially within one of outer and inner tubes. A shape-memory-alloy actuator includes a shape-memory-alloy element powered by the inductive power transfer circuit and configured to transition from a first phase to a second phase with a corresponding change in shape responsive to threshold resistive heating. A force transmission apparatus includes a locking clutch connected to the shape-memory-alloy actuator and slidably connected to another one of the outer and inner tubes. The locking clutch converts change in shape of the shape-memory-alloy element, by transition from one of the first and second phases to the other one of the first and second phases, to an extension of the inner tube from within the outer tube and prevents contraction of the inner tube into the outer tube when the shape-memory-alloy element oppositely transitions.

15 Claims, 13 Drawing Sheets

(56) References Cited

FOREIGN PATENT DOCUMENTS

| WO | 2009/015847 A1 | 2/2009 | |
|---|---|---|---|
| WO | WO-2009115645 A1 * | 9/2009 | ......... A61B 17/7216 |
| WO | WO-2011148047 A1 * | 12/2011 | ........... A61B 17/666 |
| WO | WO-2014128349 A1 * | 8/2014 | ............. A61B 17/66 |

* cited by examiner

IMPLANTABLE OSTEODISTRACTION DEVICE

FIELD

The present disclosure relates to limb lengthening devices and associated procedures used on humans to lengthen a limb such as a leg or arm.

BACKGROUND

There is a general concordance that limb-lengthening procedures are associated with considerable complications. Nevertheless, a surgery is considered as a valuable treatment option with successful outcomes. Therefore, limb length discrepancy and short stature are treated with various surgical bone lengthening techniques.

Bone lengthening with external fixation was invented in 1950s and it has remained the golden standard globally. Lengthening with external fixators are associated with complications such as pain, pin track infections, joint stiffness due to limited possibility to do rehabilitation, and refractures due to early removal of the frame. External fixation also leads to poor cosmetic outcome and frames are not practical in patients' daily life.

To overcome the problems of the external fixation, limb lengthening with intramedullary lengthening nails was developed and has gained popularity during the last decade. While internal lengthening is much more convenient for patients and can overcome the above listed problems, device related complications and technical problems continue to exist. Such reported problems are (i) implant corrosion and wear particle release (e.g., PRECICE by NuVasive ("Precice") and FITBONE by Orthofix ("Fitbone")), (ii) mechanical breakage of the nails (Precice), (iii) poor control of lengthening rate (Intramedullary Skeletal Kinetic Distractor ("ISKD")), (iv) breakages of separate antennas (Fitbone), (v) tissues irritation due to antenna placed in soft tissue (Fitbone), (vi) strong magnets leading to hazards in home environment (Precice), (vii) lengthening rate dependent on to thickness of the soft tissue (Precice), (viii) bulky home care appliance which is difficult for the patient to position correctly (Precice), (ix) no possibilities to remotely monitor patient compliance (all) and (x) limitation of the rehabilitation due to strict weight bearing limits (all).

SUMMARY

Some embodiments of the present disclosure are directed to an implantable osteodistraction device includes an outer tube, an inner tube disposed at least partially within the outer tube, an inductive power transfer circuit, a shape-memory-alloy actuator, and a force transmission apparatus. The inductive power transfer circuit connected to and at least partially within one of the outer and inner tubes, and configured to receive power through inductive coupling to an external power coil. The shape-memory-alloy actuator connected to and at least partially within the one of the outer and inner tubes. The shape-memory-alloy actuator includes a shape-memory-alloy element electrically connected to be powered by the inductive power transfer circuit. The shape-memory-alloy element is configured to transition from a first phase to a second phase with a corresponding change in shape responsive to threshold resistive heating. The force transmission apparatus includes a one-way linear movement locking clutch connected to the shape-memory-alloy actuator and slidably connected to another one of the outer and inner tubes. The one-way linear movement locking clutch is configured to convert change in shape of the shape-memory-alloy element, by transition from one of the first and second phases to the other one of the first and second phases, to an extension of the inner tube from within the outer tube and to prevent contraction of the inner tube into the outer tube when the shape-memory-alloy element transitions from the other one of the first and second phases to the one of the first and second phases. In other embodiment a ratcheting mechanism may be used to transition from one of the first and second phases to the other one of the first and second phases.

Some other embodiments are directed to an osteodistraction system that includes an inductive power unit or Home Care Unit and an implantable osteodistraction device. The inductive power unit includes at least one processor and a power supply configured to be controlled by the at least one processor to provide a controlled current level to an inductive power coil. The implantable osteodistraction device includes an outer tube, an inner tube disposed at least partially within the outer tube, an inductive power transfer circuit, a shape-memory-alloy actuator, and a force transmission apparatus. The inductive power transfer circuit is connected to and at least partially within one of the outer and inner tubes, and configured to receive power through inductive coupling to the transmitting coil or inductive power coil of the inductive power unit. The shape-memory-alloy actuator is connected to and at least partially within the one of the outer and inner tubes. The shape-memory-alloy actuator includes a shape-memory-alloy element electrically connected to be powered by the inductive power transfer circuit. The shape-memory-alloy element is configured to transition from a first phase to a second phase with a corresponding change in shape responsive to threshold resistive heating. The force transmission apparatus includes a one-way linear movement locking clutch connected to the shape-memory-alloy actuator and slidably connected to another one of the outer and inner tubes, the one-way linear movement locking clutch configured to convert change in shape of the shape-memory-alloy element, by transition from one of the first and second phases to the other one of the first and second phases, to an extension of the inner tube from within the outer tube and to prevent contraction of the inner tube into the outer tube when the shape-memory-alloy element transitions from the other one of the first and second phases to the one of the first and second phases.

Some other embodiments are directed to a method that includes operating an inductive power transfer circuit to receive power through inductive coupling from the transmitting coil, where the inductive power transfer circuit is connected to and at least partially within one of an outer tube and an inner tube disposed at least partially within the outer tube. The method further includes providing a shape-memory-alloy actuator connected to and at least partially within the one of the outer and inner tubes, where the shape-memory-alloy actuator includes a shape-memory-alloy element electrically connected to be powered by the inductive power transfer circuit. The shape-memory-alloy element is configured to transition from a first phase to a second phase with a corresponding change in shape responsive to threshold resistive heating. The method further includes providing a force transmission apparatus including a one-way linear movement locking clutch connected to the shape-memory-alloy actuator and slidably connected to another one of the outer and inner tubes. The one-way linear movement locking clutch is configured to convert change in shape of the shape-memory-alloy element, by transition from one of the first and second phases to the other one of the first and second phases, to an extension of the inner tube from within the outer tube and to prevent contraction of the inner tube into the outer tube when the shape-memory-alloy element transitions from the other one of the first and second phases to the one of the first and second phases.

Other implantable osteodistraction devices, osteodistraction systems, and corresponding methods according to embodiments of the inventive subject matter will be or become apparent to one with skill in the art upon review of the following drawings and detailed description. It is intended that all such additional implantable osteodistraction devices, osteodistraction systems, and methods be included within this description, be within the scope of the present inventive subject matter, and be protected by the accompanying claims. Moreover, it is intended that all embodiments disclosed herein can be implemented separately or combined in any way and/or combination.

DESCRIPTION OF THE DRAWINGS

Aspects of the present disclosure are illustrated by way of example and are not limited by the accompanying drawings. In the drawings.

DETAILED DESCRIPTION

Figure 1:
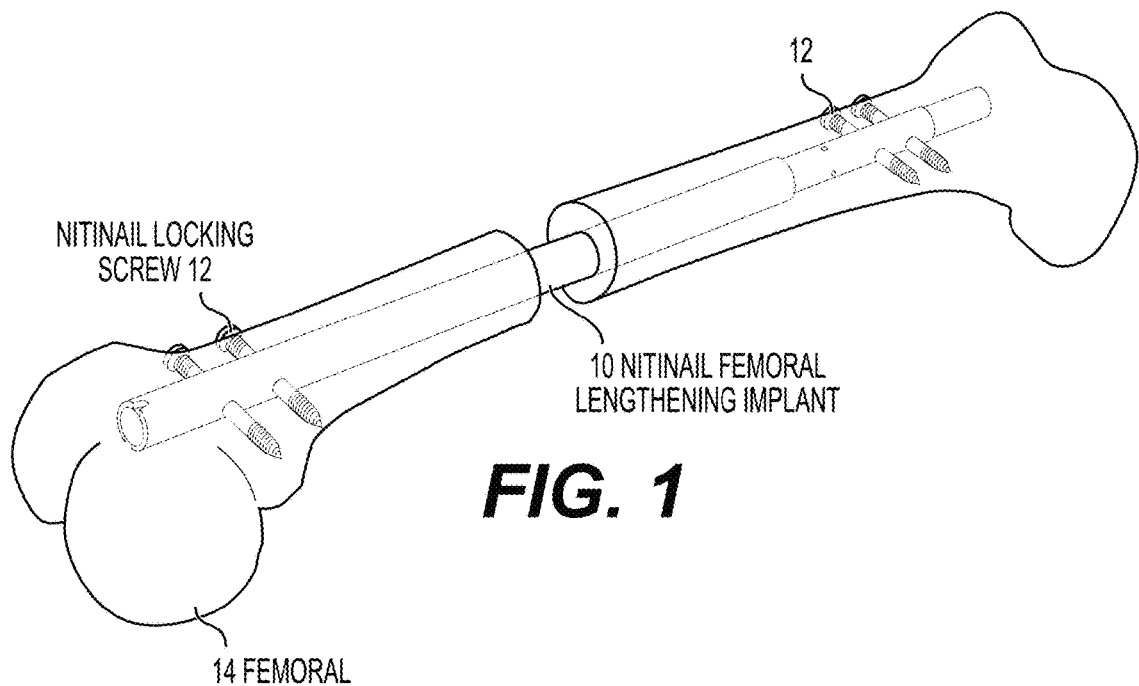
FIG. 1 illustrates a Nitinail femoral lengthening implant which is implanted in a femoral bone and secured using locking screws, and configured in accordance with some embodiments.

The following discussion is presented to enable a person skilled in the art to make and use embodiments of the present disclosure. Various modifications to the illustrated embodiments will be readily apparent to those skilled in the art, and the principles herein can be applied to other embodiments and applications without departing from embodiments of the present disclosure. Thus, the embodiments are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the embodiments. Skilled artisans will recognize the examples provided herein have many useful alternatives and fall within the scope of the embodiments.

It is to be understood that the present disclosure is not limited in its application to the details of construction and the arrangement of components set forth in the description herein or illustrated in the drawings. The teachings of the present disclosure may be used and practiced in other embodiments and practiced or carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

To overcome various problems with external fixation, limb lengthening using intramedullary lengthening nails was developed and has gained popularity during the last decade. While internal lengthening is more convenient for patients and can overcome various of the above-described problems, device related complications and technical problems continue to exist. Reported problems can include (i) implant corrosion and wear particle release (Precice and Fitbone), (ii) mechanical breakage of the nails (Precice), (iii) poor control of lengthening rate (ISKD), (iv) breakages of separate antennas (Fitbone), (v) tissues irritation due to antenna placed in soft tissue (Fitbone), (vi) strong magnets leading to hazards in home environment (Precice), (vii) lengthening rate dependent on to thickness of the soft tissue (Precice), (viii) bulky home care appliance which is difficult for the patient to position correctly (Precice), (ix) no ability to remotely monitor patient compliance (all), and (x) limitation of the rehabilitation due to strict weight bearing limits (all).

Embodiments of the present disclosure are directed to limb lengthening systems and apparatuses which may overcome one or more problems associated with other internal lengthening nails. Some embodiments are described in the context of a Nitinail System by SYNOSTE which is part of Globus Medical, Inc., although these and other embodiments are not limited to the example Nitinail System and apparatus configurations disclosed herein.

Nitinail System can be used for lengthening femur bones, tibia bones, and/or other skeletal bones to, for example, remedy limb length discrepancy caused by traumatic shortening, congenital deformities, and tumor resection.

The Nitinail System may include 5 sub-components: 1) Nitinail implant which operates as a telescopic distraction nail; 2) locking screws which are bone screws for fixing the Nitinail implant to a bone; 3) a surgical kit which is a set of specific surgical instruments used for implantation and explantation; 4) aHome Care Unit which is a remote control for wireless activation of the Nitinail implant lengthening; and 5) a lengthening protocol software 40 (FIG. 4) which is software that supports setting up prescribed activation schedules for the patient's home care use of the device during the distraction phase.

Figure 2:
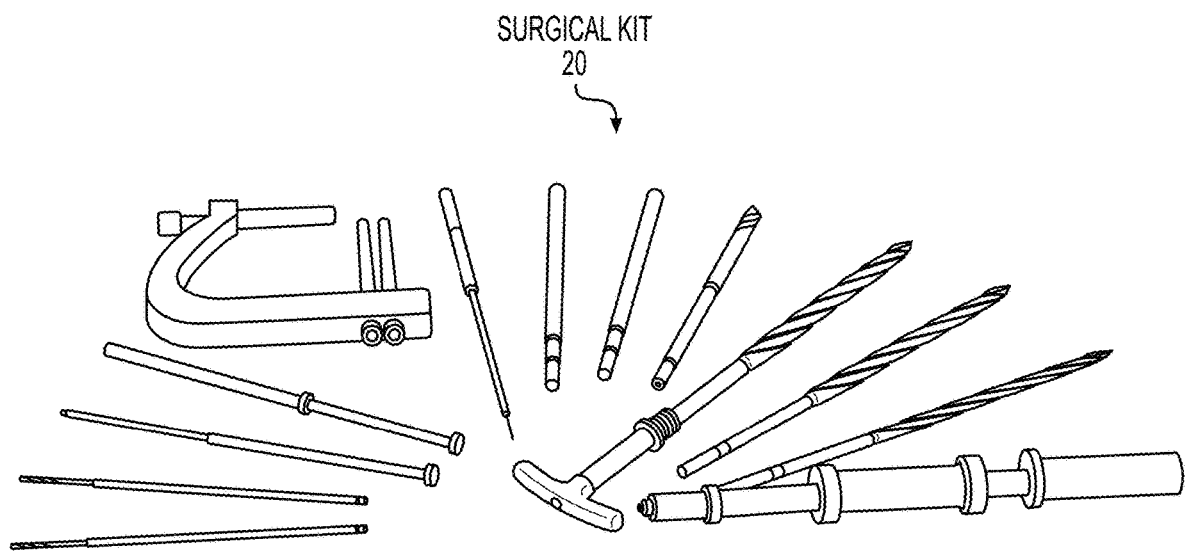
FIG. 2 illustrates tools of a surgical kit that may be used with other tools available in an orthopedic surgery room to implant the femoral lengthening implant into the femoral bone and to secure the locking screws, in accordance with some embodiments.
Figure 3:
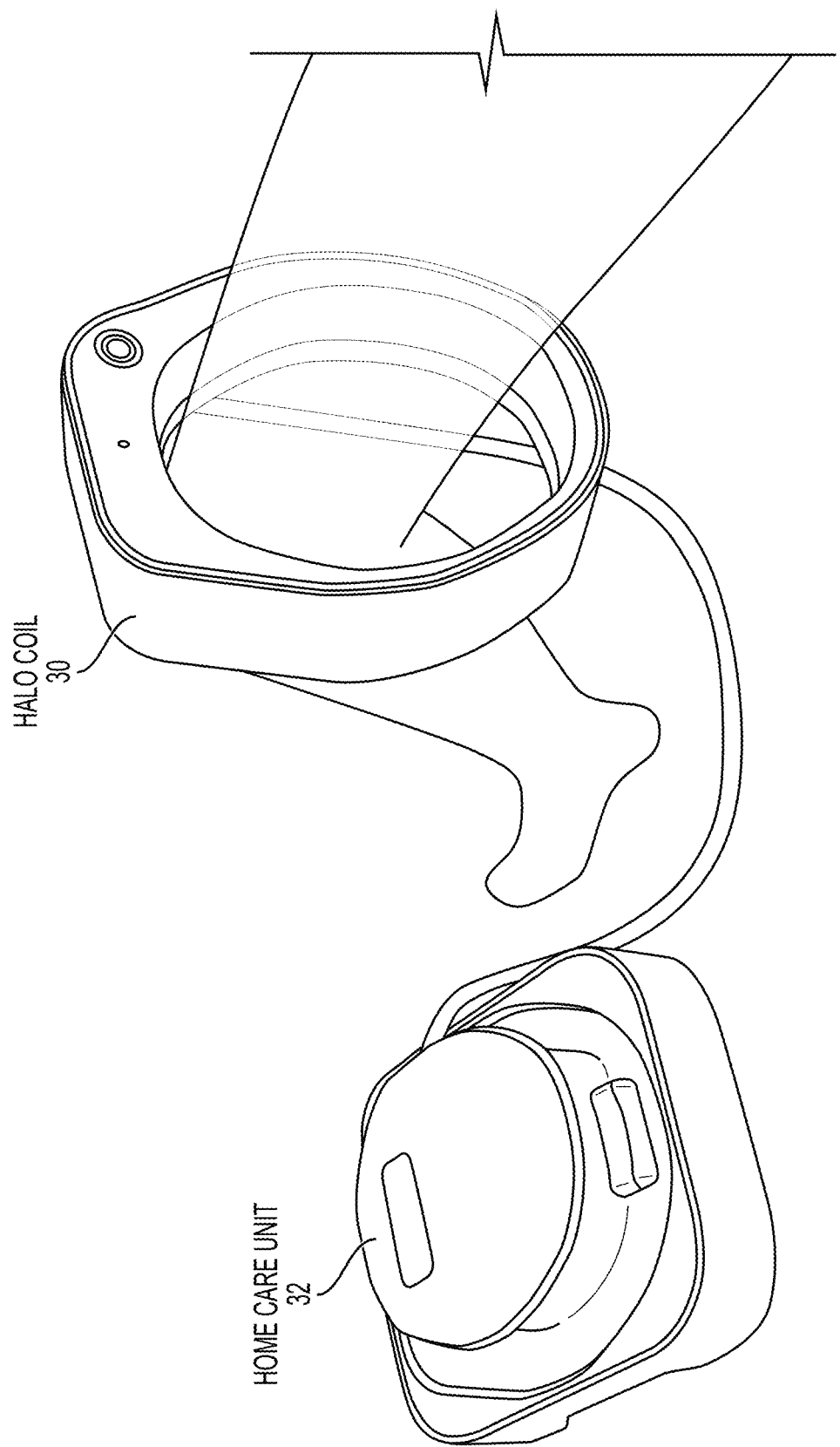
FIG. 3 illustrates a home care unit which controls a transmitting coil transmitting coil which is positioned adjacent to an inductive power transfer unit of the Nitinail implant in accordance with some embodiments.

FIG. 1 illustrates a Nitinail femoral lengthening implant 10 ("Nitinail implant" or "implant") which is shown implanted in a femoral bone 14 and secured using locking screws 12, and configured in accordance with some embodiments. FIG. 2 illustrates tools of a surgical kit 20 that may be used with other tools available in an orthopedic surgery room to implant the femoral lengthening implant 10 into the femoral bone 14 and to secure the locking screws 12, in accordance with some embodiments. FIG. 3 illustrates a home care unit 32 which controls a transmitting coil which is positioned adjacent to an inductive power transfer unit of the Nitinail implant 10. Although various embodiments of implants are explained in the context of femoral lengthening, they may be used to lengthen arms and other skeletal structure.

The home care unit 32 is an electronic device that can be used in a hospital and at patient's home to activate a lengthening mechanism of the Nitinail implant 10. The unit 32 may be also used in the operating room during the implantation to verify implant function and to perform an initial lengthening of the Nitinail implant 10. The Nitinail implant 10 is activated via resonant inductive power transfer by placing the Transmitting coil 30 around the treated leg or arm and aligned with a receiving antenna of the Nitinail implant 10. The resonant inductive transfer can be performed by near field wireless transmission of electric energy between magnetically coupled coils, which are tuned to resonate at the same frequency or any selected frequency. As will be explained below, the transmitting coil 30 is briefly operated to inductively power a force transmission device of the femoral lengthening implant 10 which applies a prescribed level of internal axial force to the femoral bone 14 and causes a prescribed rate of lengthening thereof. Repetitive operation of the implant 10 during each of a plurality of prescribed days can provide a desired lengthening of the femoral or other limb.

The home care unit 32 may be configured to communicate data through wireless (e.g., WiFi, Bluetooth, 4G/5G/NR cellular, etc.) and/or wired connections (e.g., Ethernet) and wide area networks (e.g., Internet) to a networked server for monitoring by patients, care givers, and/or healthcare professionals. The data may contain the time stamps of use, how well the positioning has been made, where the home care unit 32 is geographically located, and patient reported outcome measures such as pain level. The surgeon may also program new prescription i.e. lengthening schedule to the home care unit 32 to control movement of the Nitinail implant 10. The data may include information measured or determined from the Nitinail implant 10 such as forces acting on the implant 10 or implant length. For example, the home care unit 32 and the Nitinail implant 10 may both include a wireless communication circuit that is provides a telemetric link between the home care unit 32 and the Nitinail implant 10, to enable measurement of certain implant parameters (e.g. length, load sharing, impedance measurement, quality of regenerated bone), to enable surgeons' control over the long treatment and thus potentially improving treatment outcomes.

Figure 4:
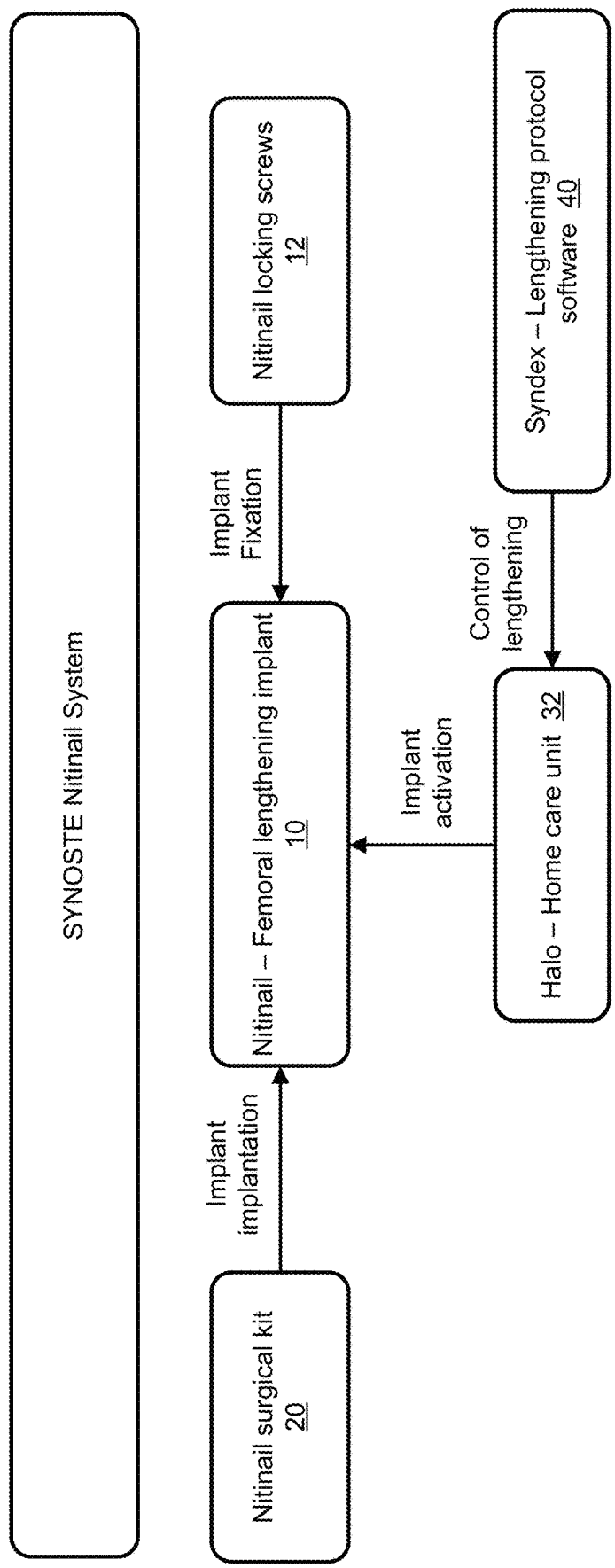
FIG. 4 illustrates a block diagram of components of the Nitinail System in accordance with some embodiments.

FIG. 4 illustrates a block diagram of components of the Nitinail System, including the surgical kit 20, the Nitinail femoral lengthening implant 10 (also "Nitinail" or "Nitinail implant" for brevity), the locking screws 12, the home care unit 32, and the Syndex lengthening protocol software 40 (also "Syndex software" for brevity) which is executed by at least one processor of at least one computing platform to perform operations in accordance with some embodiments. For example, some operations of a lengthening protocol software 40 may be performed by processor(s) of the home care unit 32 and other operations may be performed by a networked computer which provides a robust interface for a medical professional to monitor and control operation of the Nitinail implant 10 and progression of the lengthening process of the patient.

The activation of the lengthening mechanism of the Nitinail implant 10 is performed using the home care unit 32, both at the hospital and in home care. The software is used to control the lengthening by providing the patient with a schedule for the activations to be done in a form of a patient diary.

Figure 5:
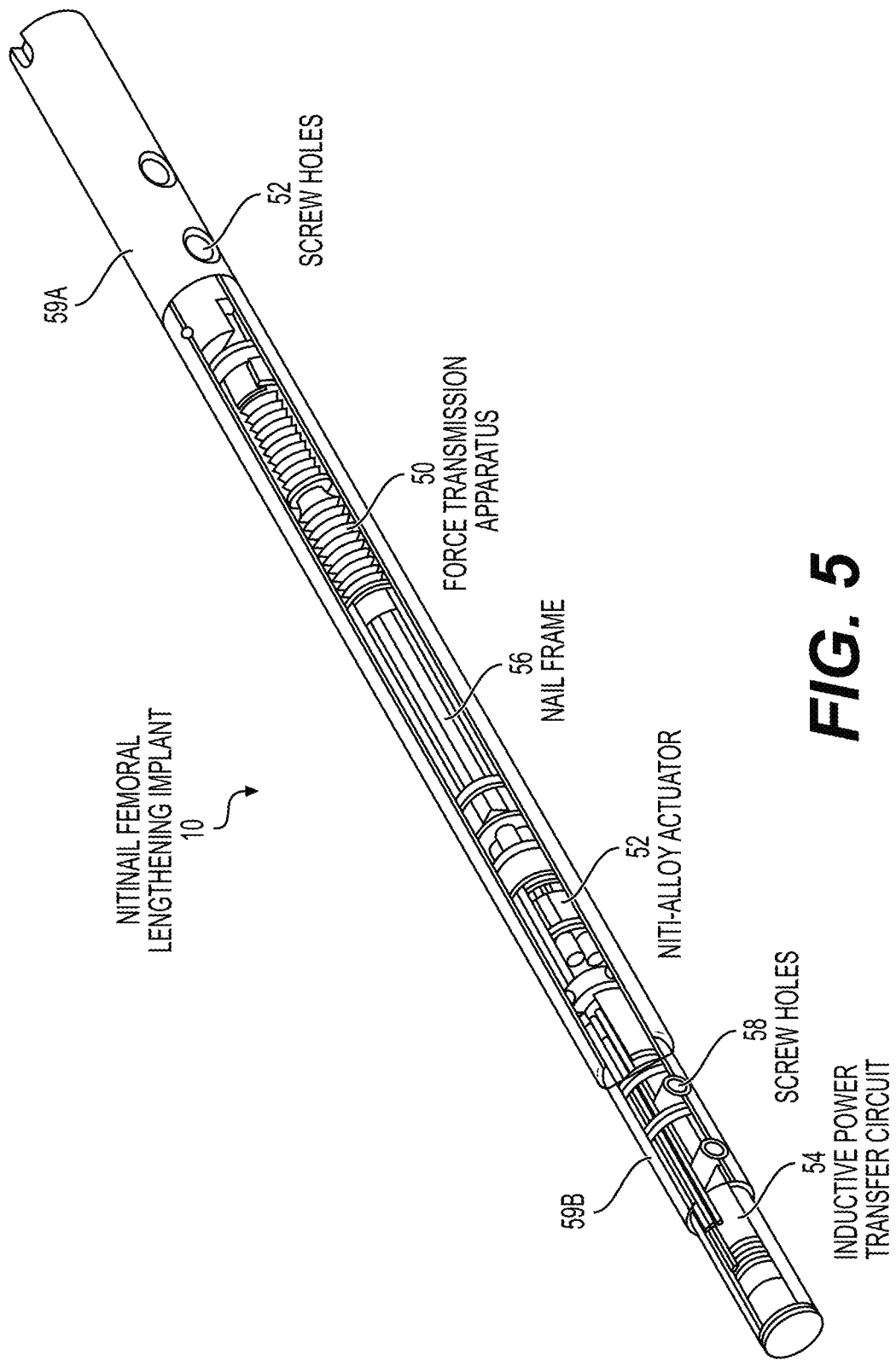
FIG. 5 illustrates four main components of the Nitinail implant which operate to cause lengthening in accordance with some embodiments.

The Nitinail implant 10 is configured as an intramedullary nail, which in one embodiment can have a maximum outer diameter of 14 mm and varying starting length and lengthening capability based on a configured variant, such as: one variant having a 50 mm lengthening capability from a 305 mm starting length; and another variant having a 70 mm lengthening capability from a 325 mm starting length. The function of the Nitinail implant 10 is based on the use of Nitinol, precise coupling of phase change shape of the Nitinol to mechanical movement, and energy transfer for activation of the Nitinol by inductive power transfer from the transmitting coil 30. FIG. 5 illustrates some main components of the Nitinail implant 10 which operate to cause mechanical lengthening in accordance with some embodiments.

Referring to FIG. 5, four main components of the Nitinail implant 10 are:

1) An inductive power transfer circuit 54 including an antenna configured to receive power through inductive coupling from the transmitting coil 30 (inductive power transfer), and which operates to convert power of an alternating magnetic field to an alternating electric current (AC);

2) A NiTi-alloy actuator 52 having NiTi-elements that operate with a two-way phase-changeable shape memory effect which is activated by resistive heating of the NiTi-elements responsive to the AC current from the inductive power transfer circuit 54;

3) A force transmission apparatus 50 forming a friction based one-way linear movement locking clutch which, in one embodiment, includes friction based locking stacks that are connected through a nail frame 56 to be moved by change in shape of the NiTi-elements and provide force transmission that causes telescopic lengthening of the implant 10 in a stepper motor-like manner; and 4) Screw fixation through pairs of screw holes 58 (screws 12 in FIG. 1 are not shown) extending through spaced apart end regions of the Nitinail implant 10 to be attached to and transfer the nail lengthening to the osteotomized bone gap.

The functioning of the different components of the Nitinail implant 10 are explained in more detail in the following sections. The inductive power transfer circuit 54 converts the electromagnetic field received from the Transmitting coil 30 into an AC electric current that flows through the NiTi-alloy actuator 52 to heat and change shape of the NiTi-elements through phase change of the NiTi material therein. The NiTi material is a metallic alloy of nickel and titanium, where the two elements may be present in roughly equal atomic percentages. The shape memory properties are dependent on the particular atomic composition of the metallic alloy. The two-way phase-changeable shape memory effect is a reversible phenomenon, also called two-way shape memory effect (TWSME), is caused by NiTi transforms between martensite and austenite phases. During the memory effect phase transformation from martensite to austenite the NiTi is able to generate movement that is utilized by the Nitinail implant 10 as a work energy to extend its length. The phase transformation from martensite to austenite starts at a defined temperature, As, and is complete at a defined temperature Af. The transformation back to martensite from austenite is initiated at a defined temperature, Ms, and is complete at a defined temperature Mf. The phase transformation exhibits a hysteresis behavior with the relation of temperatures being: Mf<As<Ms<Af. The power transferred by the Transmitting coil 30 is controlled by the home care unit 32 to cause resistive heating of the NiTi-elements and trigger the phase change thereof which triggers a defined distraction rate target by the Nitinail implant 10.

Although some embodiments of the present disclosure discuss use of a NiTi-alloy actuator, other embodiments are not limited to use of NiTi material since other shape memory alloys (SMAs) may be used which change shape responsive to heating which is obtainable through power provided by inductive coupling such as described herein.

The amount of TWSME movement generated by the alloy is affected by: 1) prestress, 2) load imposed on the alloy during phase transformation, and 3) degree of transformation at the end of the transformation. The prestress is a stress imposed on the NiTi alloy in its martensite phase before phase transformation to austenite and used to assist the transformation from austenite to martensite.

The Transmitting coil 30 and home care unit 32 can be configured to transform 50-60 Hz, 100-240 V power from conventional power outlet or power supplied by a battery to a RF energy transfer signal with a frequency of, e.g., 258 kHz within a tolerance of +/−4 kHz. During the energy transfer the Transmitting coil 30 is aligned with the receiving antenna of the inductive power transfer circuit 54. In practice this means putting the Transmitting coil 30 around the patient's thigh close to the knee. The energy transfer signal is transmitted via the Transmitting coil 30 transmitting coil.

Figure 6:
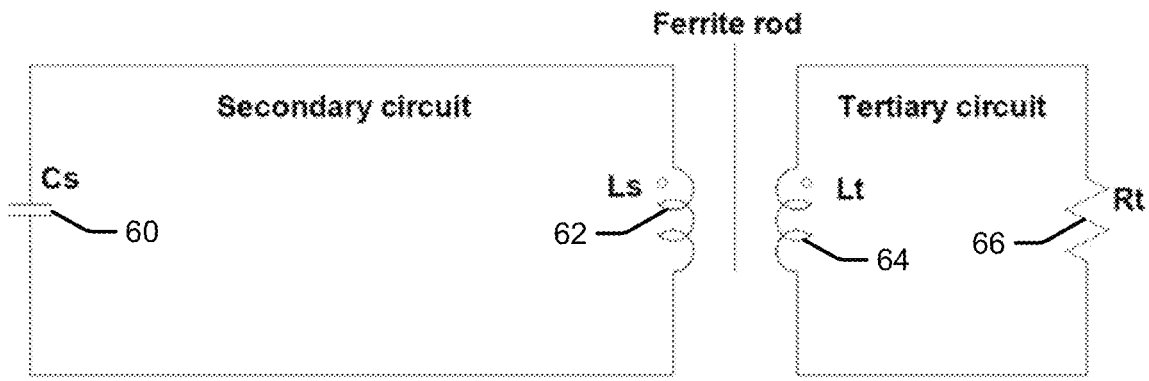
FIG. 6 illustrates a circuit diagram of the receiving antenna including a secondary circuit and a tertiary circuit linked inductively in accordance with some embodiments.

FIG. 6 illustrates a circuit diagram of the receiving antenna including a secondary circuit and a tertiary circuit linked inductively in accordance with some embodiments. Its function is to receive the power transmitted by Transmitting coil 30 and to transfer it to the tertiary circuit. A secondary winding 62, which may be copper Litz wire, is wound on top of a coil former. A ferrite rod is inserted inside the coil former to focus the magnetic field through the winding 62. The ferrite rod may also form at least a part of the coil former. A capacitor 60 is attached at the end of the coil former in series with the winding 62. The whole secondary circuit is encapsulated inside a leak free seamless glass package. A trifilar (three wires in parallel) tertiary winding 64 is wound directly on top of the glass encapsulation. By coupling with the secondary circuit, an induced current is led to the NiTi-elements (Rt) 66 of the NiTi-alloy actuator 52 via biocompatible conductors. The tertiary winding 64 may be made of biocompatible silver wire insulated with poly(ether urethane). The secondary and tertiary windings coaxially wound around the ferrite rod function essentially as a transformer. The current in the tertiary circuit may be specified to be maximum of, e.g., 14.75 A. Accordingly in FIG. 6, the term Cs 60 represents the secondary circuit series resonant tank capacitor, the term Ls represents the secondary circuit winding, the term Lt represents the tertiary winding, and the term Rt represents the resistive load of the NiTi-elements of the NiTi-alloy actuator 52.

Referring again to FIG. 5, the NiTi-alloy actuator 52 functions through the NiTi elements being repetitively activated (heated through current flow) in a controlled manner. Heating of the NiTi elements causes change in their shape which is configured to generate a stroke in the axial direction of the Nitinail implant 10. The NiTi elements (NiTi wires) are heated by conducting the current through them for a time period of time, e.g., 4 s. In one embodiment, a group of NiTi wires are crimped together to form one active element that works in unison. The wires are mechanically and electrically in parallel in the bundle, leading to increased actuation performance and decreased electrical resistance when compared to a single wire. In a further embodiment, the bundle has 7×D0.381 mm wires with a distance of 20 mm between the crimps.

A martensite-to-austenite phase transformation occurs in the NiTi elements induced by the heating of NiTi above its transformation temperature (about 70-120° C. depending on opposing load), which causes the NiTi elements to contract, producing a high force. The NiTi-alloy actuator 52 converts the contraction of the NiTi elements to a radial stroke along the Nitinail implant 10. The contraction of NiTi elements and thus the stroke depends on the opposing load and varies between, e.g., 1-7% of wire length. The stroke pushes directly the rods of the Nitinail implant 10 apart from each other via a friction based one-way linear movement locking clutch of the force transmission apparatus 50. When the NiTi is cooled back to the initial temperature, e.g., below the transformation temperature, the NiTi returns to martensite phase and is ready for another actuation or stroke.

The NiTi elements are thermally isolated from the nail frame 56 with, e.g., polymeric tubing or air gap to reduce or prevent immediate conduction of the thermal energy to the implant surface. Some degree of implant surface warming occurs locally in the proximity of the NiTi elements for a short period of time after an actuation. However the thermal mass of the Nitinail implant 10 is sufficient to keep the heating in acceptable bounds.

The force transmission apparatus 50 in FIG. 5 operates to convert and transmit the repeated stroke of the NiTi-alloy actuator 52 to a step wise one-way axial lengthening of the Nitinail implant 10. The force transmission apparatus 50 also carries the axial loads subjected on the Nitinail implant 10. Force transmission includes two friction-based one-way linear movement locking clutches, a moving one and a fixed one, and a square rod. The two locking clutches and the rod form an inchworm type of an actuator, which is actuated by the stroke of the NiTi-alloy actuator 52. The NiTi-alloy actuator 52 is attached to the movable locking clutch. The fixed clutch is attached to the inner tube of the nail frame 56. The square rod is attached to the outer tube of the nail frame 56. As the NiTi-alloy actuator 52 actuates, it forces the movable locking clutch to move forward, the clutch grips ("locks") the square rod and forces it to move through the fixed locking clutch thus causing the telescopic Nitinail implant 10 to extend. Thus the Nitinail implant 10 lengthens one minute step distance. In one embodiment, the locking clutch is configured as a stack of 10 identical locking levels, which allow a square rod to move in one direction, but prevent the movement into the other with small rollers being wedged between the rod's surface and the tilted wall of the locking level.

The nail frame 56 comprises the inner tube and the outer tube and functions to carry the bending and torsional (in combination with force transmission apparatus 50) loads imposed on the Nitinail implant 10, fixing it to the treated bone and protecting the other implant components from penetration of bodily fluids. The nail frame 56 acts as the outer surface of the Nitinail implant 10. The illustrated nail frame 56 has telescoping outer and inner tubes 59A and 59B. The nail frame 56 may be formed from a cobalt chrome alloy, MP35N, ASTM F 562, which is less prone to crevice corrosion. Two locking screws 12 are inserted in the proximal and distal ends of the Nitinail implant 10 in a mediolateral orientation. The configuration of the locking screws 12 allows establishing a stable fixation. The screw fixation is responsible for transferring the lengthening of the Nitinail implant 10 to a separation of the osteotomy gap. The parts of the nail frame 56 act as a housing for the rest of the parts of the Nitinail implant 10 and shield them from the incursion of body fluids by utilizing e.g. lip seals or o-rings.

Figure 7:
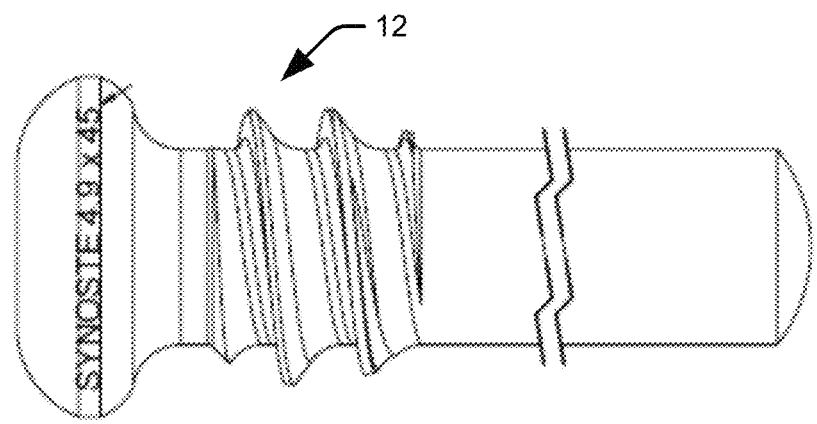
FIG. 7 illustrates a portion of a locking screw which is configured in accordance with one embodiment.

FIG. 7 illustrates a portion of a locking screw 12 which is configured in accordance with one embodiment. The locking screw 12 contain a self-tapping thread for the proximal cortex, a hexagonal socket (e.g., 3.5 mm) and an inner thread for attachment to a screwdriver for easier implantation and explantation. The locking screw 12 may be from titanium grade 5. or cobalt chrome.

Figure 8:
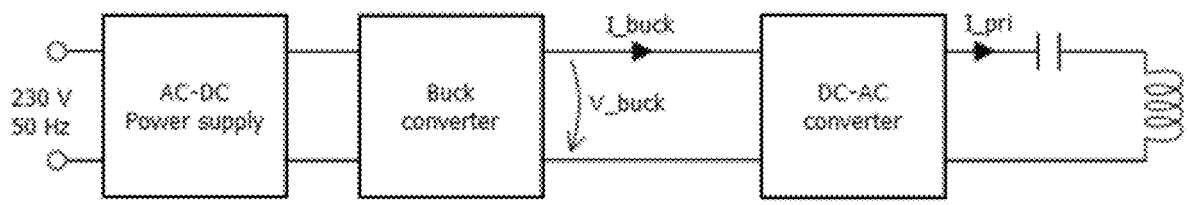
FIG. 8 illustrates a circuit diagram of the home care unit and connected Transmitting coil which operate to transmit power to the inductive power transfer circuit of the Nitinail implant in accordance with some embodiments.

FIG. 8 illustrates a circuit diagram of the home care unit 32 and connected Transmitting coil 30 which operate to transmit power to the inductive power transfer circuit 54 of the Nitinail implant 10, in accordance with some embodiments. Referring to FIG. 8, wireless energy transfer from the Transmitting coil 30 to the inductive power transfer circuit 54 is based on resonant inductive power transfer. In order to achieve power delivery to Nitinail implant 10, the Transmitting coil 30 has an AC current (I_pri) w which in turn generates an AC magnetic field that further enables wireless power transfer to the Nitinail implant 10. The circuit features an adjustment of the transmitted power that ensures that the correct amount of power is delivered into the Nitinail implant 10 regardless of the position of the Nitinail implant 10 inside the Transmitting coil 30, as long as the implant 10 remains in the area where treatment is possible (which may be indicated to a user by an LED or other visible and/or audio device which is selectively activated in the Transmitting coil 30) and the Transmitting coil 30 is operated within the specified operating conditions. Detection of the position of a receiving antenna of the Nitinail implant 10 in relation to the electromagnetic field generated by a transmitting antenna of the Transmitting coil 30 may be determined by sensing the changes in the Impedance of the primary coil of the Transmitting coil 30. The magnetic field generated by the Transmitting coil 30 couples to the receiving antenna of the inductive power transfer circuit 54 and provides the power necessary for the functioning of the NiTi-alloy actuator 52.

The home care unit 32 includes at least one processor circuit ("processor") which executes program instructions from at least one memory, and may further include a removable memory module port, e.g., SD-card slot, that can be used to provide an indication to the processor to switch the device between operation in surgeon mode and patient mode. The difference between the modes may include the following: patient mode has a time limit of, e.g., 20 minutes between activations; and surgeon mode has a time limit of, e.g., 10 minutes between activations. The daily limit on amount of activations may be, e.g., 10 in the patient mode and, e.g., 30 in the surgeon mode. The purpose of the surgeon mode is to facilitate more effective use in the operating room and hospital premises.

The lengthening protocol software 40 can be a web based application intended for planning and tracking of the distraction osteogenesis treatment with Nitinail System. The software 40 is used by the orthopedic surgeons performing the distraction osteogenesis treatment with Nitinail System. Additionally, the software includes an admin mode, where the users (surgeons) and implants may be managed. In one embodiment, there is no direct interface between the software 40 and other parts of Nitinail System. However, the software 40 takes in critical implant information that is required for operation of the algorithm, as well as other key information, such as expiry date. The critical information includes the individually measured performance characteristics as well as the maximum lengthening of each Nitinail implant. Additionally, the software 40 allows to allocate implants to particular surgeons, which minimizes the risk of selecting the wrong Nitinail implant.

In various embodiments, the software 40 can operate to create periodical distraction plans so as to meet the surgeon's distraction rate targets (mm/day). The software 40 takes as input the lengthening performed in the last control period, measured from X-rays or other measurements apparatus within the Nitinail implant 10, and the number of activations performed, based on the patients markings in a patient diary. Based on this information, and information provided by surgeon, the software 40 calculates a treatment plan for the next period (usually 1 week), that targets to surgeon-provided target distraction rate. Additionally, the software 40 provides a printable patient diary, automatically created according to the calculated plan, that provides the patient means to easily follow the prescription as well as to keep track of the performed activations. The whole treatment, with all the events, are saved into the software 40, which enables the surgeon to view the treatment progress as well as to edit incorrect data. A summary sheet containing all the key information from the treatment may be printed and stored to patient records once the treatment is completed. The software 40 may provide a surgeon mode which allows planning and control of treatment, and an admin mode which allows adding of surgeons and implants, and other administrative functions. The algorithm logic of the software 40 can operate to adjust the number of activations per day based on measurements of lengthening in previous lengthening period(s), which may be measured through x-ray analysis.

Accordingly, in some embodiments, the processor is configured to control a power supply of the home care unit 32 to provide a controlled current level to the Transmitting coil 30 (an inductive power coil). In a further embodiment, the processor is configured to control the power supply through a power conversion unit to provide the controlled current level to the Transmitting coil 30 for a first defined time duration sufficient to transition the shape-memory-alloy element from the first phase to the second phase with the corresponding change in shape, and to thereafter prevent the power supply from providing the controlled current level to the Transmitting coil 30 for at least a second defined time duration sufficient to transition the shape-memory-alloy element from the second phase to the first phase with a corresponding reversal in the change in shape. In a further embodiment, the home care unit 32 includes a network interface configured to communicate through a communication network. The processor is configured to generate a patient treatment diary tracking time of day for each occurrence of the power supply being controlled to transition the shape-memory-alloy element from the first phase to the second phase with the corresponding change in shape, and to communicate the patient treatment diary through the network interface, such as to a remote network server which is monitored by the surgeon. In another further embodiment, the processor is configured to receive a prescribed activation schedule through the network interface and to control the power supply to provide the controlled current level to the Transmitting coil 30 according to the prescribed activation schedule.

Example configuration of various components of the Nitinail implant 10 are now explained in accordance with some embodiments.

As explained above and with reference to FIGS. 3 and 5, the Transmitting coil 30 is powered to provide wireless energy transfer to the inductive power transfer circuit 54 via inductive coupling. The inductive power transfer circuit 54 provides current through the NiTi-alloy actuator 52 to resistively heat the NiTi elements. The heating causes the occurrence of TWSME by the Nitinol elements, and the TWSME pushes a rod ("push rod") to move the clutch and the force transmission apparatus 50, to move the telescoping outer tube 59A relative to the telescoping inner tube 59B. Consecutive inductive activations cause the push rod to move back and forth repeatedly, provided that sufficient cool down of the NiTi elements is allowed.

The force transmission apparatus 50 comprises a one-way linear movement locking clutch that is connected to the NiTi-alloy actuator 52 via the push rod of the nail frame 56. The TWSME movement of the NiTi-alloy actuator 52 causes the one-way linear movement locking clutch to move. In some embodiments, as the clutch moves, it grabs hold of a square rod. This causes some amount of elastic backlash that is dependent on the external load and decreases the amount of actuation achievable by the telescopic step motor function of the NiTi-alloy actuator 52. The square rod in turn moves through another linear one-way linear movement locking clutch that is fixed to the frame of the force transmission apparatus 50. The square rod is attached to the outer tube and the clutch. The back and forth movement of the TWSME movement of the NiTi-alloy actuator 52 causes the telescoping part to move and increase its length. When the TWSME movement of the NiTi-alloy actuator 52 is reversed during cooling making it shorter, the one-way linear movement locking clutch engages in the locking direction preventing shortening of the Nitinail implant 10, aside from the elastic backlash that occurs due to the loading.

Figure 9:
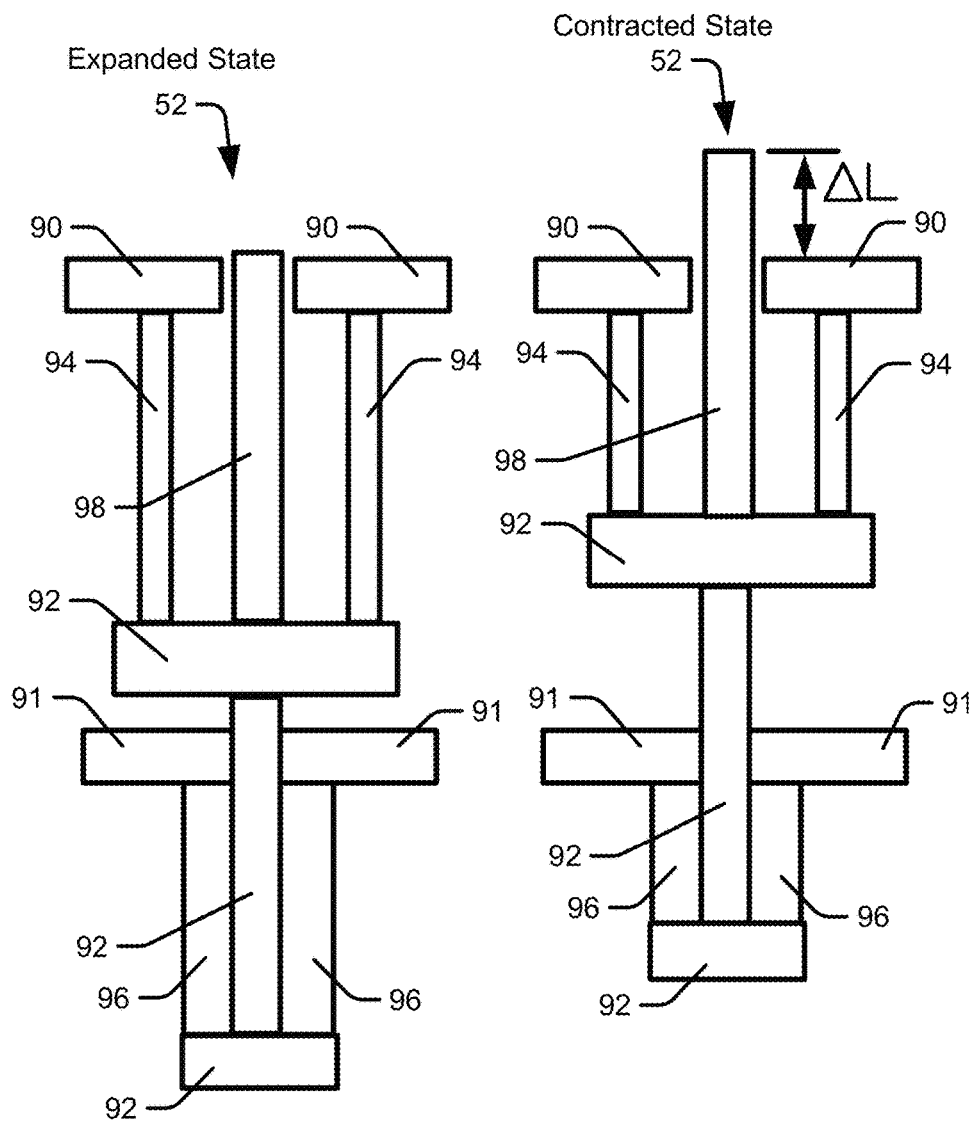
FIG. 9 illustrates a simplified structural representation of the NiTi-alloy actuator shown in a non-activated expanded state (left) and in a activated contracted state (right) in accordance with some embodiments.

FIG. 9 illustrates a simplified structural representation of the NiTi-alloy actuator 52 shown in a non-activated expanded state (left) and in an activated contracted state (right), or vice versa depending upon the original shape memory of the shape-memory-alloy, in accordance with some embodiments. As explained above the NiTi-alloy actuator 52 operates through the TWSME of the Nitinol elements 94. The Nitinol elements 94 are configured to have TWSME transformation through current provided by the inductive power transfer circuit 54 while energized by the Transmitting coil 30. When the actuator 52 is in the non-activated state, the Nitinol elements 94 are in the martensite (cold) phase and, in which, they are expanded. While in the martensite phase a prestress spring 96 is used to apply a prestress to the Nitinol elements 94, e.g., to help expand (lengthen) the elements 94. The purpose of the prestress is to increase the actuation performance of the NiTi-alloy material of the Nitinol elements 94 and to assist in transformation back to martensite phase from the austenite (hot) phase. The heating of the NiTi-alloy material above the austenite start temperature (As) initiates the transformation from martensite to austenite phases. Once the austenite finish (Af) temperature is reached the NiTi-alloy material is fully in the austenite form, and the Nitinol elements 94 are in the contracted state (FIG. 9 right side), or vice versa depending upon the original shape memory of the shape-memory-alloy. When the NiTi-alloy material starts to cool down and reaches the martensite start (Ms) temperature the transformation back to the marten site phase begins. This transformation is completed at the martensite finish (MO temperature, whereby the Nitinol elements 94 are in the expanded state (FIG. 9 left side), or vice versa depending upon the original shape memory of the shape-memory-alloy.

In FIG. 9, the Nitinol elements 94 may be at least one bundle of individual wires or rods made of Nitinol or any other shape-memory-alloy. The bundle of individual wires or rods are electrically connected to each other in series or in parallel and mechanically arranged in parallel, so that the contractive force via its phase transition provides a summing of the contractive force of each individual wire or rod together.

Figure 10:
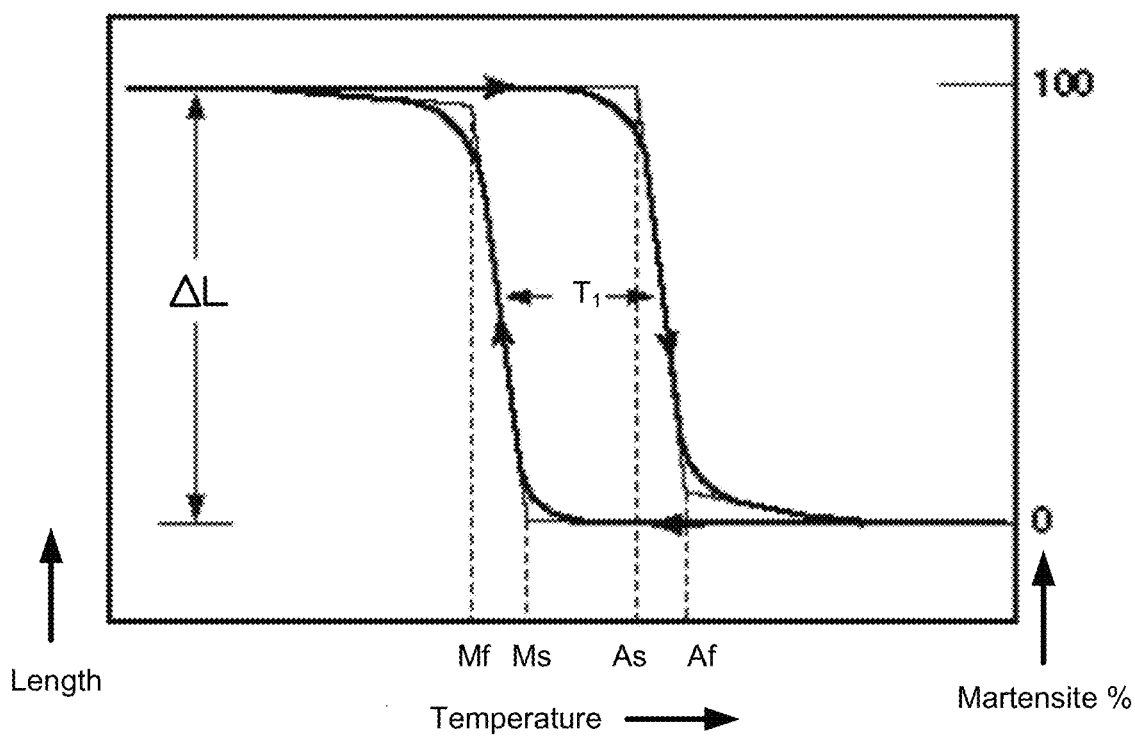
FIG. 10 illustrates a graph showing an effect of hysteresis on the transformation temperatures of a NiTi-alloy material which is used in accordance with some embodiments of the present disclosure.

FIG. 10 illustrates a graph showing an effect of hysteresis on the transformation temperatures of a NiTi-alloy material which is used in accordance with some embodiments of the present disclosure. The NiTi-alloy material exhibits a hysteresis on the transformation temperatures which means that the material has to be cooled down further than the austenite start temperature to be fully transformed back to martensite. This can be an important design factor when choosing the correct Nitinol composition to reach favorable operation inside the human body, where the minimum normal temperature reached is around 37 degrees Celsius.

The transformation from martensite to austenite phases causes the Nitinol wires used in the Nitinol elements 94 to decrease in length, or vice versa to extend in length depending upon their original shape memory, which is utilized to generate the output stroke of the actuator 52, as illustrated in FIG. 9 by the length change delta-L. The illustrated elements 90 and 91 are fixed structures which can be connected to either telescoping outer tube 59A or the inner tube, and the illustrated elements 90 and 91 are f connected to the telescoping actuator part 59B. The illustrated elements 92 are moving structures, which cause movement of the push rod 98 by expansion and contraction of the Nitinol elements 94 through the alternating between phases. The push rod 98 is connected to the force transmission apparatus 50 which contains the one-way linear movement locking clutch. Repetitive expansion and contraction of the Nitinol elements 94 causes the outer tube 59A to incrementally telescope away from the inner tube 59B. The one-way linear movement locking clutch of the force transmission apparatus 50 substantially prevents contraction movement of the outer tube 59A relative to the inner tube 59B as the Nitinol elements 94 expand after actution during cool down period.

The Nitinol wires in the Nitinol elements 94 are heated up to the transformation temperature by an electrical current in a matter of seconds. After this, the wires are allowed to cool down and they return to the martensite state aided by the prestress spring. During the length change the Nitinol elements 94 are also able to produce a force that is proportional to the surface area of the of the elements 94. The Nitinol will actuate against an external load regardless of the magnitude of load. However, the magnitude of the load affects the output stroke, delta-L in FIG. 9, and fatigue life of the Nitinol. In general, the higher the external loading, the shorter the stroke and the shorter the maximum achieved cycle life. The cycle life can be millions of cycles at a loading level of 170 MPa (depending on design) and goes down to several thousand cycles when a load level of 400-500 MPa is used.

The level of prestress caused by the prestress springs 96 has an effect on the transformation temperature, output stroke and fatigue life. In general, the higher the prestress, the higher the transformation temperature and output stroke are. Simultaneously, the fatigue life is slightly diminished. In general a prestress level of 50-70 MPa is recommended as a guideline for best performance by commercial Nitinol actuator alloy manufacturers. The effective output force of the actuator can be calculated as:

$$F(sma\_act\_out)=F(design\_stress)-F(prestress)=P(design)*A-P(prestress)*A$$

Figure 11:
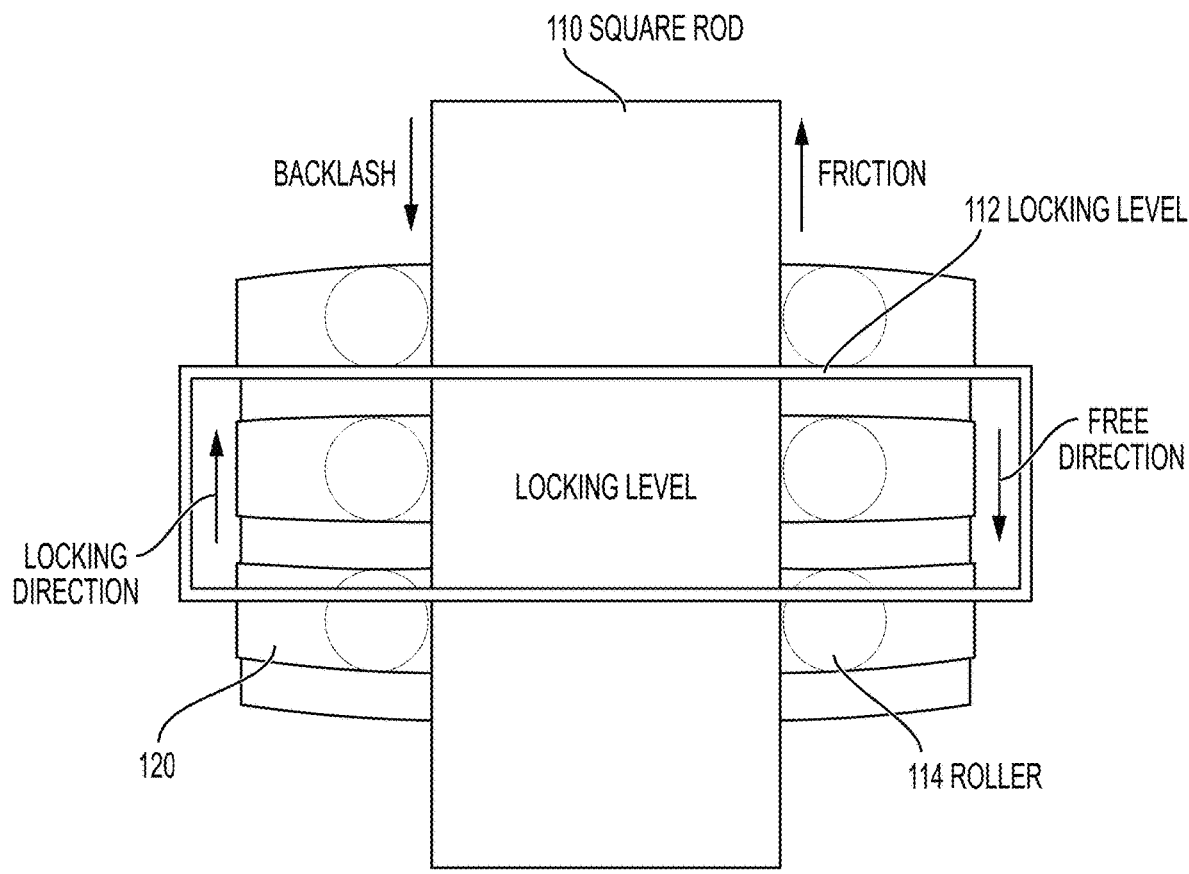
FIG. 11 illustrates a cross-sectional view of a one-way linear movement locking clutch of the force transmission apparatus which is configured in accordance with some embodiments.

FIG. 11 illustrates a cross-sectional view of a one-way linear movement locking clutch of the force transmission apparatus 50 which is configured in accordance with some embodiments. Referring to FIG. 11, the one-way linear movement locking clutch uses friction based operation to allow only one-way movement of a square rod 110 which is connected to be moved by the push rod 98 (FIG. 9). The one-way linear movement locking clutch can operate with different locking levels. Moving the square rod 110 up in the image of FIG. 11 allows it to move freely with a certain friction. In sharp contrast, pushing the square rod 110 down will cause the clutch to lock and generates a backlash. Pushing the locking level 112 down will allow it to move freely with a certain friction, while pulling the locking level 112 up will cause the clutch to lock and generates a backlash.

Figure 12:
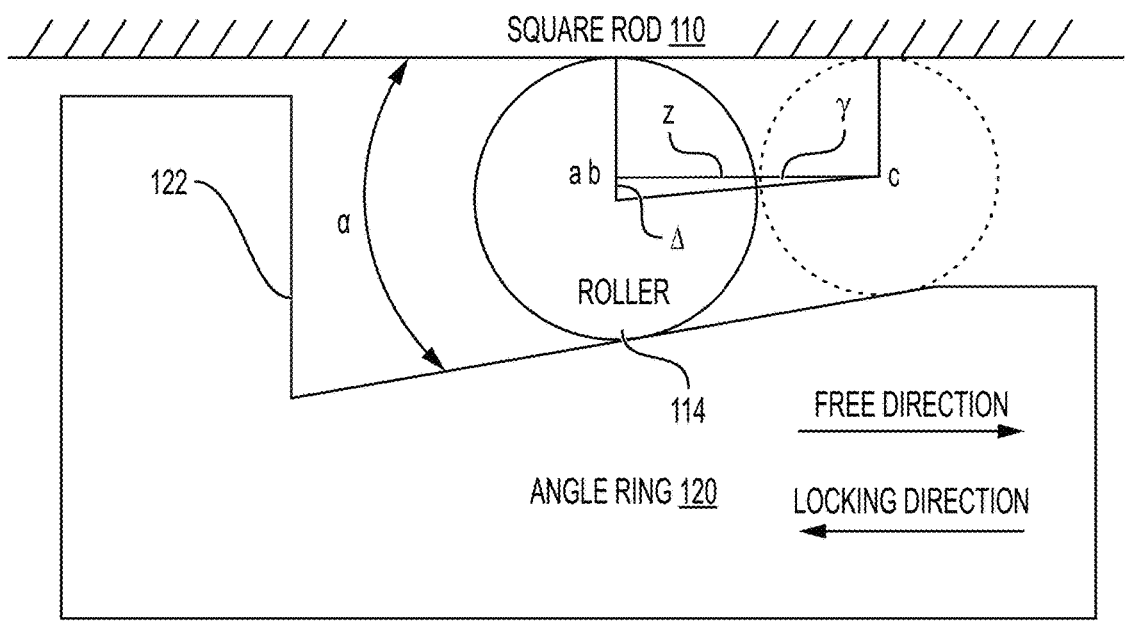
FIG. 12 illustrates a side view of the one-way linear movement locking clutch having a roller which moves along an angle ring to engage the square rod, allowing movement in a free direction while preventing movement in the locking direction, and is configured according to some embodiments.

The friction based one-way linear movement locking clutch is an apparatus that includes at least three components that generate a locking action that is based on wedging by friction forces, in accordance with some embodiments. FIG. 12 illustrates a side view of the one-way linear movement locking clutch having a roller 114 which moves along an angle ring 120 to engage the square rod, allowing movement in a free direction while preventing movement in the locking direction, and is configured according to some embodiments. The components of the one-way linear movement locking clutch include the angle rings 120 containing a slanted surface, the rollers 114 and the square rod 110. Planar springs can be used to keep the rollers 114 in contact with the square rod 110 and the angle rings 120 in all situations and a roller blocker plate 122 that prevents jams in the system.

Accordingly, in some embodiments, the one-way linear movement locking clutch of the force transmission apparatus 50 includes a rod (e.g., 92 and 98 in FIG. 9, 110 in FIG. 11, etc.) connected to a shape-memory-alloy actuator 52. At least one ring apparatus includes an angle ring and a roller, the angle ring encircling the square rodand a portion of the angle ring having a slanted surface facing the rod, the roller being positioned between the slanted surface and the rod. When the shape-memory-alloy element transitions from one phase to another which urges contraction of the inner tube 59B into the outer tube 59A, friction rolls the roller on the slated surface to become wedged between the slated surface and the rod and prevent contraction of the inner tube 59B into the outer tube 59A.

Important material parameters to limit the amount of backlash are the hardness of the material and the elastic modulus of it. To prevent damage at high external loads an important parameter is the yield strength and the hardness of the material. Additionally the backlash can be decreased and maximum load bearing capability increased by increasing the area of contact surface between the components. This can be done e.g. by increasing the number of locking levels used.

In principle, the backlash diminished by 1/N where N is the number of locking levels in the system. Also increasing the length of the rollers 114 in the system causes a similar effect and is affected by the non-idealities that arise from the non-uniform contact surfaces between the roller 114, the angle ring 120 and square rod 110. The load bearing capability of the system increases roughly to the factor of N when increasing the number of locking levels.

Furthermore the selected locking angle affects the backlash. The larger the value of the locking angle, alpha, the smaller the backlash. However increasing the angle to too high values will cause the system to not lock altogether and instead causes it to slip in the locking direction. Environmental factors also have to be considered in the selection of the locking angle as factors that may change the frictional coefficient in the system can also change the required locking angle. Typically angle values from 8-12 degrees are used. When the square rod 110 is moved into the free direction (up in FIG. 11 and to the right in FIG. 12), the rollers 114 are disengaged from wedged position and the square rod 110 can move freely. A frictional force is generated in this situation and it is mainly attributed to the normal forces generated on the roller 114 by the planar spring keeping it in contact with the angle ring.

The higher the spring force, the higher the friction. From a backlash point of view it is beneficial to have a high spring force as this increases the loading of the roller 114 against the two counter surfaces. With no loading the roller 114 forms a line contact with each counter surface and when load is being added the surface area of the contact increases rapidly and thus the backlash behavior is not linear. The initial loading steps generate the most backlash and this can be countered to a certain extend by having a preload caused by the planar spring.

As explained above, actuation of the telescopic step motor function of the NiTi-alloy actuator 52 happens when the Nitinol elements have TWSME movement and the Nitinol elements 94 contract to generate an output stroke of the push rod 98. The actuation of the push rod 98 pushes the clutch which moves the square rod 110. Once the stroke of the NiTi-alloy actuator 52 is complete, the one-way linear movement locking clutch slides with respect to the square rod 110 and the moving clutch returns to the original position pulled by the NiTi-alloy actuator 52. During actuation the external load is initially transferred from the fixed clutch to the moving clutch for the duration the NiTi-alloy actuator 52 is generating an output stroke. Once the stroke is complete and the NiTi-alloy actuator 52 starts to retract, the external load is transferred back to the fixed clutch.

The step length of the NiTi-alloy actuator 52 is given by the equation: $\Delta L = \Delta L(SMA\_act) - L(backlash)$, where L(backlash)=composite of the backlashes of the moving and fixed clutch, which is in case of two identical clutches approximately two times the backlash of an individual clutch.

The force output generated is given by the equation: $F(out) = F(sma\_act\_out) - F(friction)$, where F(friction)=sum of the frictions of the clutches and other sliding structures of the telescopic step motor. After the initial actuation the system is again ready for an actuation after an appropriate cooling time that allows the NiTi-alloy actuator 52 to be reset.

Post actuation lengthening is an operation that can cause the telescopic stepper motor function of the NiTi-alloy actuator 52 to still gain length after an actuation has been completed. This is due to the elastic nature of the backlash in the friction based one-way clutches. If the external loading on the telescopic step motor is reduced after an actuation the backlash of the fixed clutch will reduce and the telescopic step motor will gain an equal amount of length. The maximum gained length is the full backlash caused by the external loading.

The actuation of the step motor depends not only on the external load but also on the loading history of the external load. The first actuation performed after increasing the external load from zero to some desired load is called Ramp up actuation. A second activation in the same load is called the Dwell actuation, the dwell actuation is shorter (smaller actuation step length) than the ramp up actuation and all subsequent actuations after the first dwell actuation are of the same magnitude if actuations at the same external load are continued without additional loading or unloading steps. The cause for the change in the actuation length is a complex combination of the loading/unloading of the friction based one-way linear movement locking clutches and the external load being transmitted through them to the NiTi-alloy actuator 52. The difference between the ramp up and dwell actuations gets larger as the external loading is increased.

A third actuation class, clinical performance actuation, has been defined and presents the most likely loading scenario history in clinical use. This loading scenario simulates the changes in external loading that will be caused by loading of the treated leg as well as the muscles contracting and relaxing in between the actuations. This is defined as 1) first increasing the compressive load to 300 N above that of the desired actuation force, 2) then going to 100 N lower compressive force, 3) then back to 300 N higher compressive load and 4) then finally going to the desired actuation external load and actuating the step motor. The clinical performance actuation is situated between the dwell and ramp up actuations.

The actuation length of the step motor decays during the use of the step motor. This is caused by the TWSME fatigue of the Nitinol in the NiTi-alloy actuator 52. The fatigue is dependent on the external loading, prestress, actuation numbers and actuation temperatures of the Nitinol. The fatigue needs to be taken into account when structuring the requirements for the step motor. Cyclic external loading of the step motor causes minute amount of backtracking (shortening) of the step motor. The backtracking is a function of loading cycles and is attributed to the elastic and plastic deformations in the friction based one-way linear movement locking clutches and other step motor structures.

Figure 13:
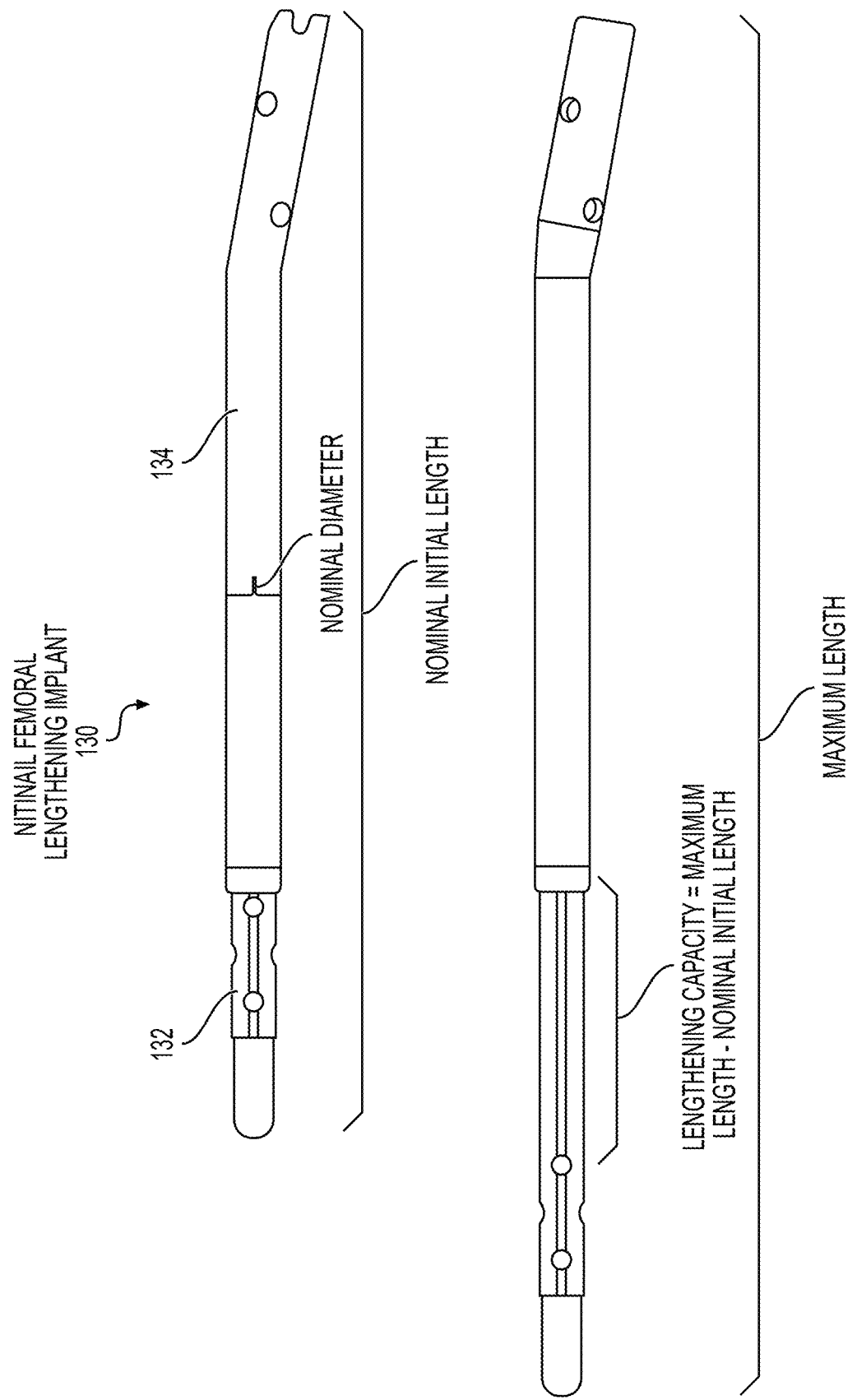
FIG. 13 illustrates two views of another Nitinail femoral lengthening implant that is configured in accordance with some embodiments.

FIG. 13 illustrates two views of another Nitinail femoral lengthening implant 130 that is configured in accordance with some embodiments. The top drawing of the Nitinail implant 130 corresponds to the nominal initial length before extension of the inner tube 132 from within the outer tube 134 is performed via cyclic alternating activations and deactivations. The bottom drawing of the Nitinail implant 130 corresponds to the maximally extended length after extension of the inner tube 132 from within the outer tube 134 has been performed via cyclic alternating activations and deactivations. The lengthening capacity of the Nitinail implant 130 is illustrated as the difference between the maximum length (bottom drawing) and the nominal initial length (top drawing). Although various embodiments are illustrated and described in the context of the inner tube 132 and outer tube 134 having a circular cross-section, these and other embodiments are not limited thereto and may have any cross-sectional shape such as oval, rectangular, square, etc.

Figure 14:
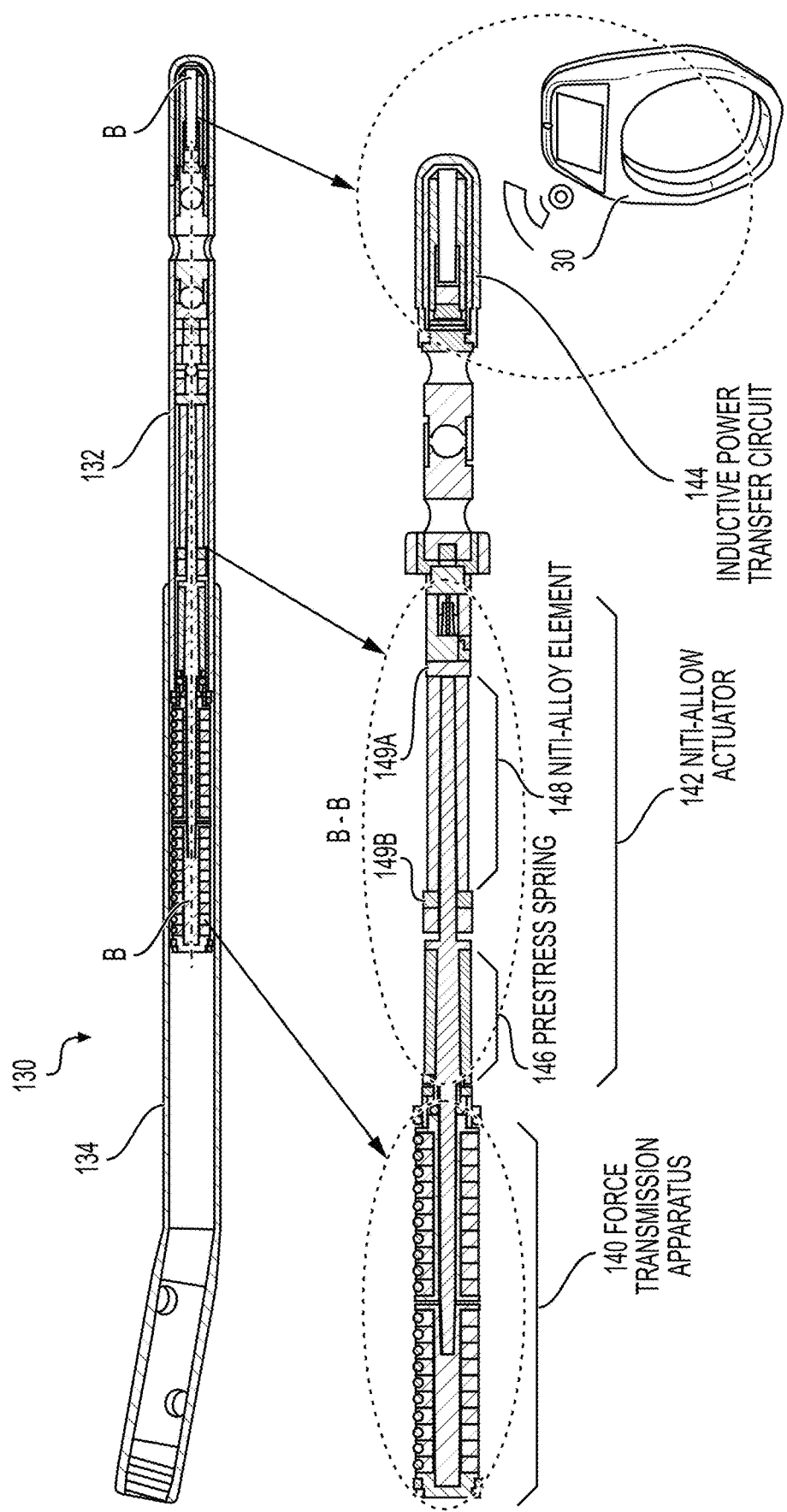
FIG. 14 illustrates two longitudinal cross-sectional drawings of the Nitinail implant of FIG. 13 that is configured in accordance with some embodiments.

FIG. 14 illustrates two longitudinal cross-sectional drawings of the Nitinail implant 130 of FIG. 13 that is configured in accordance with some embodiments. Referring to FIG. 14, the top drawing shows the longitudinal cross-sectional view of the entire Nitinail implant 130. The bottom drawing shows an expanded view between points B-B with the housing (frame) removed to facilitate view of components of the Nitinail implant 130. The components include a force transmission apparatus 140, a NiTi-alloy actuator 142, and an inductive power transfer circuit 144.

Potential advantages are provided by the Nitinail implant 130 of FIG. 14, which may include that the curved shaft, e.g., of an outer tube 134, can more easily conform to the hollowed opening formed within curved bones, such as femoral bones. In some embodiments an inner tube 132 and the outer tube 134 are curved along their lengths to conform closely to an opening created in a bone for implantation. The curved shaft may thereby enable a larger nominal diameter implant to be implanted within a curved bone when compared to use of another implant having a straight shaft, e.g., as shown in FIG. 5. Alternatively or additionally, the curved shaft may enable less bone to be hollowed-up in order to receive the implant when compared to use of another implant having a straight shaft.

Referring to FIG. 14, the inductive power transfer circuit 144 is connected to and at least partially within one of the outer and inner tubes (e.g., illustrated as within the inner tube 132), and configured to receive power through inductive coupling to the Transmitting coil 30 (e.g., an external power coil). The NiTi-allow actuator 142 (e.g., or other shape-memory-alloy actuator) is connected to and at least partially within the one of the outer and inner tubes (e.g., illustrated as within the inner tube 132). The NiTi-alloy actuator 142 includes a NiTi-alloy element 148 (e.g., or other shape-memory-alloy element) electrically connected to be powered by the inductive power transfer circuit 144. The NiTi-allow actuator 142 is configured to transition from a first phase to a second phase (e.g., from austenite phase to martensite phase) with a corresponding change in shape responsive to threshold resistive heating (e.g., as shown in FIG. 10). The force transmission apparatus 140 includes a one-way linear movement locking clutch 170 connected to the NiTi-allow actuator 142 and slidably connected to another one of the outer and inner tubes (e.g., illustrated as the outer tube 134). The one-way linear movement locking clutch 170 is configured to convert change in shape of the NiTi-alloy element 148, by transition from one of the first and second phases to the other one of the first and second phases (e.g., from austenite phase to martensite phase or vice versa), to an extension of the inner tube 132 from within the outer tube 134 and to prevent contraction of the inner tube 132 into the outer tube 134 when the NiTi-alloy element 148 transitions from the other one of the first and second phases to the one of the first and second phases (e.g., from martensite phase to austenite phase or vice versa).

Figure 15:
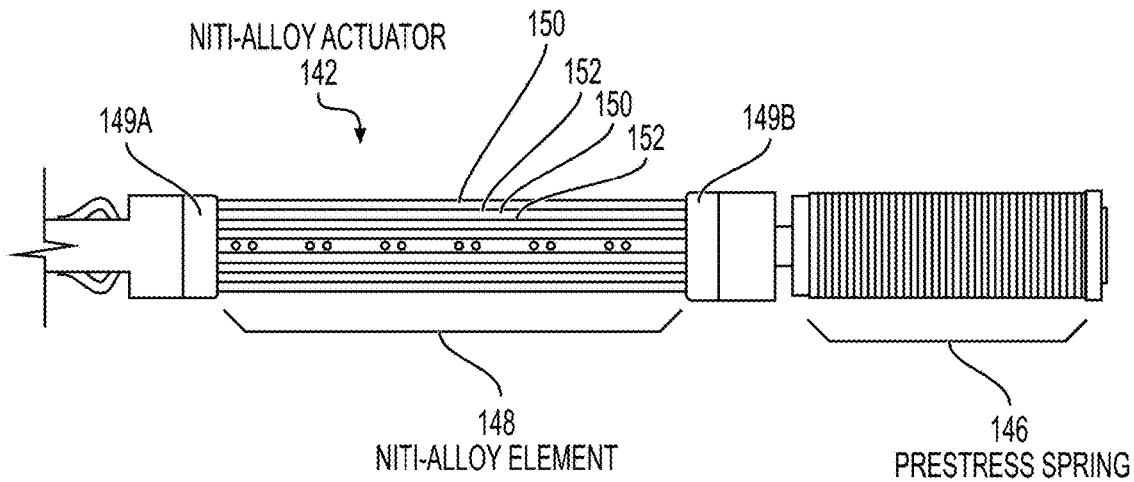
FIG. 15 illustrates an enlarged view of the NiTi-alloy actuator shown in FIG. 14 and configured in accordance with some embodiments.

In the embodiment illustrated in FIGS. 14 and 15, a prestress spring 146 is attached between the NiTi-alloy element 148 and the force transmission apparatus 140, and configured to apply tensile force to the NiTi-alloy element 148 to promote extension of the NiTi-alloy element 148 when transitioning from the other one of the first and second phases to the one of the first and second phases (e.g., from martensite phase to austenite phase or vice versa).

Figure 17A:
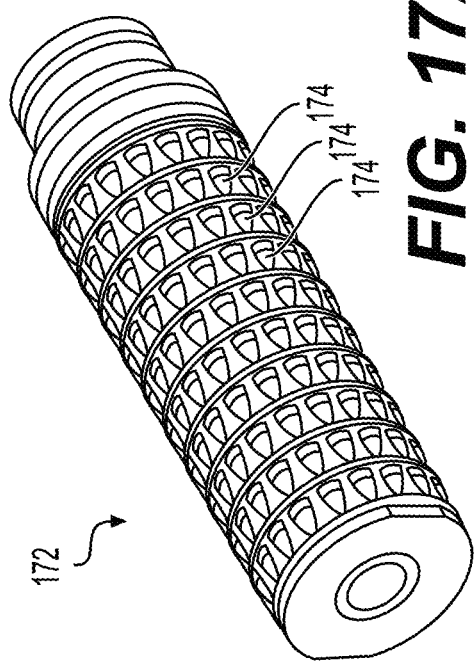
FIG. 17A illustrates an isometric view of the one-way linear movement locking clutch of the force transmission apparatus configured according to some embodiments.
Figure 17B:
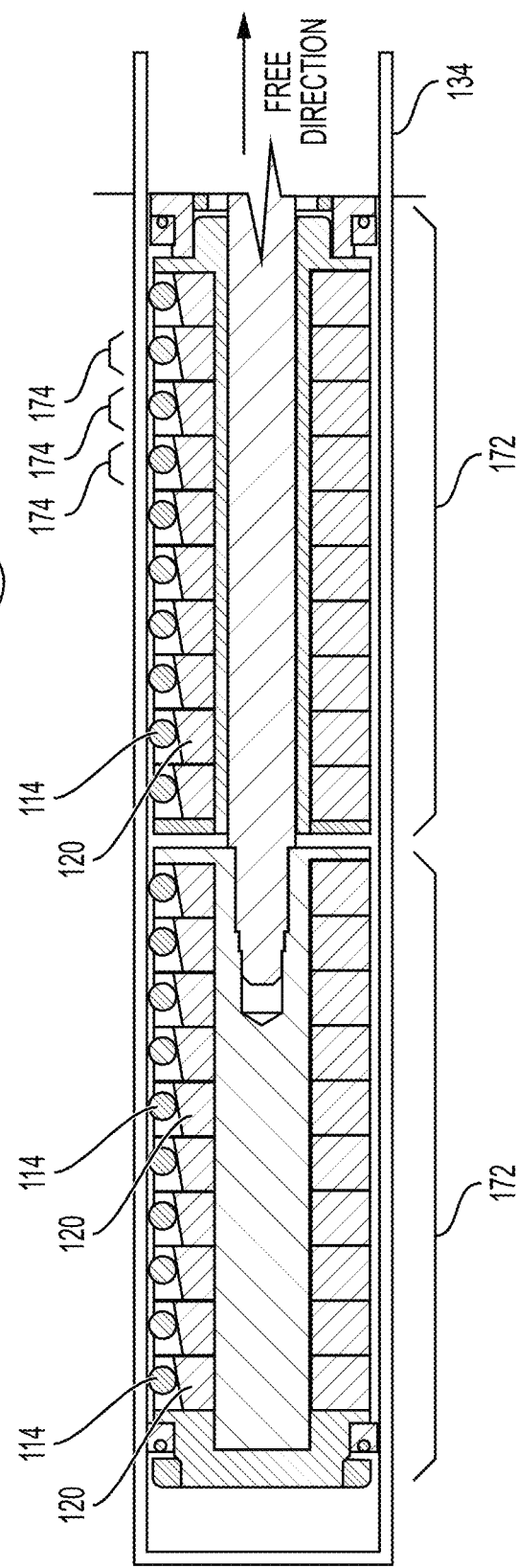
FIG. 17B illustrates a cross-sectional view of the one-way linear movement locking clutch of FIG. 17A configured according to some embodiments.

FIG. 17A illustrates an isometric view of a component 172 forming part of the one-way linear movement locking clutch 170 of the force transmission apparatus 140 configured according to some embodiments. FIG. 17B illustrates a cross-sectional view of an assembled pair of the components 172 forming the one-way linear movement locking clutch 170 configured according to some embodiments. In the illustrated embodiment, each of the components 172 of the one-way linear movement locking clutch 170 includes a stacked set, e.g., 10, of the angle rings 120 and associated rollers, spheres, balls, or barrels 114.

In one embodiment, the one-way linear movement locking clutch 170 of the force transmission apparatus 140 includes at least one ring apparatus including an angle ring 120 and a roller 114. At least one portion of the angle ring 120 has a slanted surface relative to and facing an inner surface of the other one of the outer and inner tubes (e.g., illustrated as the outer tube 134), and with roller being positioned between the slanted surface and the inner surface of the other one of the outer and inner tubes (e.g., outer tube 134). When the NiTi-alloy element 148 transitions from the other one of the first and second phases to the one of the first and second phases (e.g., from martensite phase to austenite phase or vice versa), which urges contraction which pushes the clutch forward which girps the inner surface o the outer tueb, which then extends the telescope, In the illustrated embodiment, the one-way linear movement locking clutch 170 includes a plurality of the ring apparatuses, and a rod 176 extending through a center opening of the angle rings 120 of the plurality of the ring apparatuses to arrange the angle rings 120 along a major axis of the one of the outer and inner tubes. The rod 176 is attached to the NiTi-alloy actuator 142.

In the embodiment illustrated in FIG. 17A, the ring apparatus includes a plurality of surface recesses 174 in the angle ring 120 that are spaced apart circumferentially around the angle ring 120 and have the slanted surface, and a plurality of rollers 120 are positioned in different ones of the surface recesses 174.

The roller may be a spherical ball, a cylinder, or another shape that can be frictionally moved to provide the one-way linear movement locking clutch described herein.

The one-way linear movement locking clutch 170 is configured to convert change in shape of the NiTi-alloy element 148 (e.g., shape-memory-alloy element), by transition from the first phase to the second phase (e.g., when transitioning from austenite phase to martensite phase or vice versa), to an extension of the inner tube 132 from within the outer tube 134 and to prevent contraction of the inner tube 132 into the outer tube 134 when the NiTi-alloy element 148 transitions from the second phase to the first phase (e.g., when transitioning from martensite phase to austenite phase or vice versa).

The angle ring 120 surface is inclined in reference to outer tube 134 so that pushing the rod 176 in the locking direction (leftward movement of rod 176 in FIG. 17B) causes the roller 114 to wedge between the angle ring 120 and the inner surface of the outer tube 134. The value of the angle needed to jam the roller 114 is based on the friction coefficients between the materials used in the construction. As the locking occurs the external force applied to the rod 176 generates a backlash in the system. The backlash is caused by elastic properties of the materials.

FIG. 15 provides an enlarged view of the NiTi-alloy actuator 142 shown in FIG. 14 and configured in accordance with some embodiments. Referring to FIG. 14, the NiTi-alloy actuator 142 includes a NiTi-alloy element 148 and a prestress spring 146.

The NiTi-alloy actuator 142 includes a plurality of NiTi-alloy rods 150 (e.g., or other rod-shaped shape-memory-alloy elements) extending between a first member 149A and a spaced apart second member 149B. The first member 149B is connected to and at least partially within the one of the outer and inner tubes (e.g., illustrated as within the inner tube 132. The rods may have a circular cross-section, oval cross-section, square cross-section, or other shape. The second member 149A is connected to the one-way linear movement locking clutch 170 of the force transmission apparatus 140, e.g., which is connected to the clutch via the rod that extends through the presteress spring. The prestress spirng is supported against tube 149 as illustrated in FIGS. 14 and 15.

The NiTi-alloy rods 150 comprise a Nitinol alloy of nickel and titanium. The NiTi-alloy actuator 142 can include a plurality of elastic rods 152, e.g., a metal or other elastic material having sufficient strength, extending between the first member 149A and the second member 149B. The elastic rods 152 may be arranged interspersed with the NiTi-alloy rods 150. The first member 149A and the second member 149B may include clamping plates having openings configured to receive and fixedly clamp to opposite ends of the elastic rods 152 and the NiTi-alloy rods 150.

The prestress spring 146 can be attached between the second member 149B and the force transmission apparatus 140 and configured to apply tensile force to the NiTi-alloy rods 150 to promote extension of the NiTi-alloy rods 150 when transitioning from the second phase to the first phase (e.g., when transitioning from martensite phase to austenite phase or vice versa).

Figure 18:
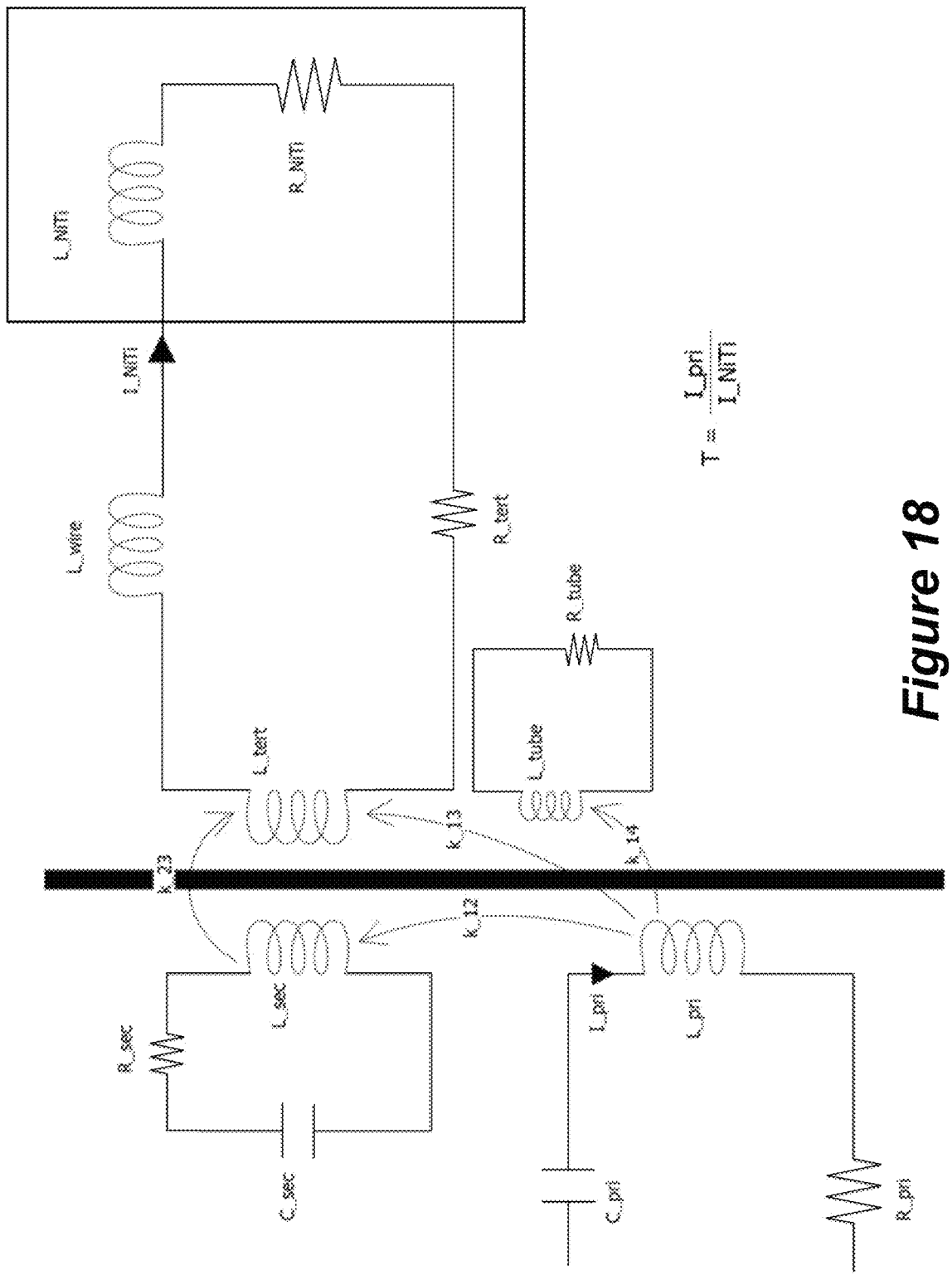
FIG. 18 illustrates a circuit diagram of the functioning of the wireless energy transfer in accordance with some embodiments.

As explained above, the wireless energy transfer in the in Nitinail System is based on resonant inductive power transfer. FIG. 18 illustrates a circuit diagram of the functioning of the wireless energy transfer in accordance with some embodiments. Referring to FIG. 18, an AC signal is fed into the primary LC circuit (L_pri & C_pri). At resonant frequency, the reactive components of C_pri and L_pri cancel each other, essentially reducing the impedance of the primary circuit to R_pri. The current in inductor L_pri induces an AC magnetic field at the resonant frequency of LC circuit. The generated magnetic field couples to the secondary circuit (k_12), which consists of a resonant circuit tuned to a specific frequency. The coupling induces a current that further generates a magnetic field that is opposite to the magnetic field generated by the primary. The secondary further couples to tertiary (k_23) via the generated magnetic field, thereby inducing a current into the tertiary circuit. The current induced to tertiary leads to heating of the NiTi wires (R_NiTi). The primary magnetic field additionally couples directly to tertiary (k_13) and Nitinail implant's 10 metal housing (k_14). The coupling to the metal housing leads to eddy currents in the metal tube of the implant 10, which lead to increase in its temperature (losses).

The performance of the power transfer system is highly dependent on the selection of correct values for each components. Additionally, variance in the components from nominal values may have a significant impact on the overall performance. Hence particular parameters in the circuit need to be controlled. Given that all of the components have some innate variance, the overall performance optimization of the system includes 1) Optimization for performance (efficiency P_tert/P_pri) and 2) Optimization for robustness. The latter includes designing the circuits so that the system's performance is not sensitive to particular individual parameters. Additionally, the design needs to take into account some limitations that are set by e.g. patient safety (High voltages, magnetic field strength . . . ), component restrictions (rated voltage & current of C_sec etc.) and physical size restrictions.

The selection of the components in the primary essentially define the operating frequency of the whole energy transfer system. The inductance of the primary (L_pri) and the current I_pri flowing in it correspondingly define the strength of the generated magnetic field. Also the number of turns and the cross sectional area of the primary coil are important design parameters. Additionally, the value of R_pri defines the resistive losses in the primary and together with L_pri defines the Q-value of the primary circuit.

The combination of secondary and tertiary needs to be designed so that it resonates at a meaningful frequency relative to the primary magnetic field. This frequency is not necessarily exactly equal to the operating frequency of the primary. In the receiving circuit (secondary and tertiary), losses (not including the intended losses at NiTi) are induced mainly by resistive losses in secondary (R_sec), resistive losses in tertiary (R_wire), eddy current losses in tube and losses in ferrite. In order to control the losses in the NiTi, also these losses need to be controlled.

The position between the primary and secondary winding is not fixed. Hence the coupling k_12 can vary significantly when Nitinail implant 10, i.e., the inductive power transfer circuit 54, is moved within the primary coil of the Transmitting coil 30. Generally a better coupling is achieved near the edge of the primary coil. Correspondingly a worse coupling is achieved at the center of the coil. If not compensated for, the changing coupling could lead to significantly different current in tertiary. The coupling k_12 can be observed by the home care unit 32 as change in the ratio of V_DC, I_Dc, and R_DC). A higher coupling increases the load seen by the buck converter and correspondingly a lower load is seen with lower coupling. The minimum R_buck is observed when there is no load within the primary winding. The relationship between the coupling and R_buck can be used to compensate for the current delivered to the NiTi load. At the highest coupling (high R_buck), I_buck may be reduced and at the lowest coupling it may be increased to achieve a current close to nominal in the Niti load.

Figure 16:
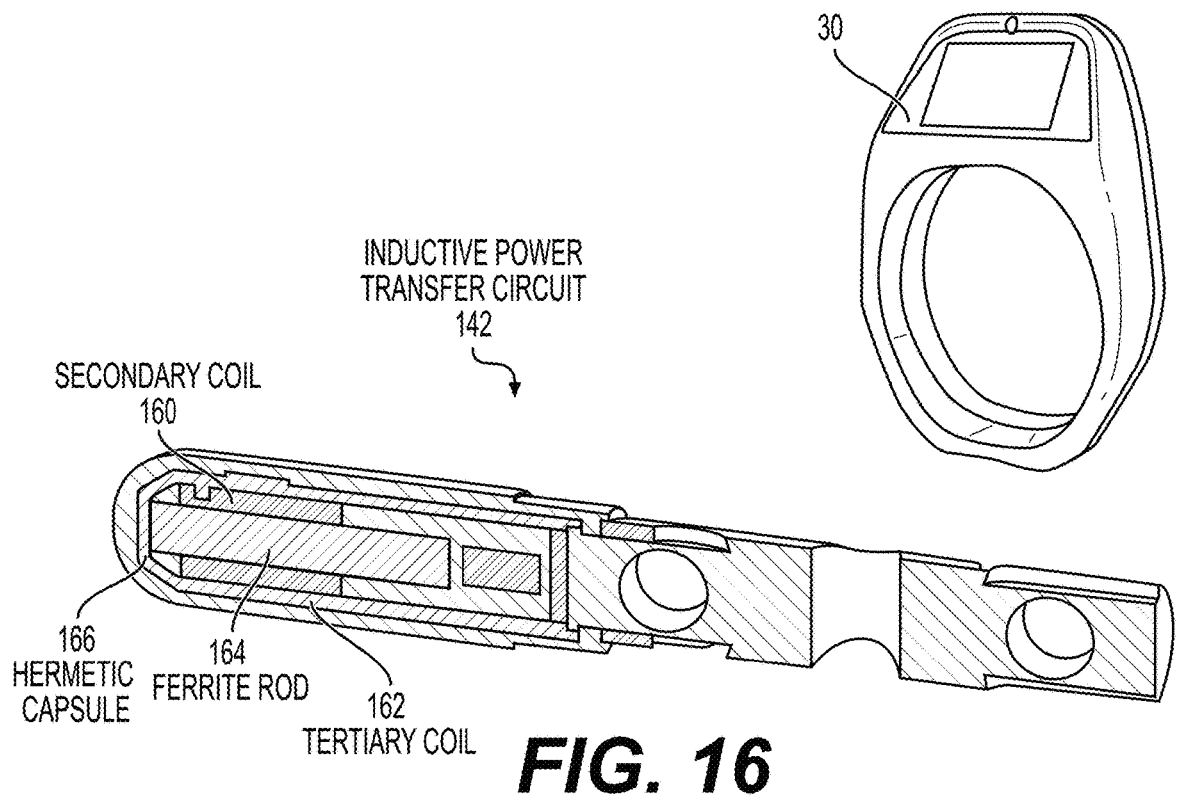
FIG. 16 illustrates a cross sectional view of the inductive power transfer circuit which is configured in accordance with some embodiments.

FIG. 16 illustrates a cross sectional view of the inductive power transfer circuit 142 which is configured in accordance with some embodiments. The inductive power transfer circuit 142 includes a secondary coil 160 and a tertiary coil 162 which are wound around and further inductively coupled by a ferrite rod 164. These components are enclosed in a hermetic or other type of leak free capsule 166 to prevent bodily fluids from contaminating the inductive power transfer circuit 142.

Further Definitions and Embodiments

In the above-description of various embodiments of present inventive concepts, it is to be understood that the terminology used herein is for the purpose of describing particular embodiments only and is not intended to be limiting of present inventive concepts. Unless otherwise defined, all terms (including technical and scientific terms) used herein have the same meaning as commonly understood by one of ordinary skill in the art to which present inventive concepts belongs. It will be further understood that terms, such as those defined in commonly used dictionaries, should be interpreted as having a meaning that is consistent with their meaning in the context of this specification and the relevant art and will not be interpreted in an idealized or overly formal sense expressly so defined herein.

When an element is referred to as being "connected", "coupled", "responsive", or variants thereof to another element, it can be directly connected, coupled, or responsive to the other element or intervening elements may be present. In contrast, when an element is referred to as being "directly connected", "directly coupled", "directly responsive", or variants thereof to another element, there are no intervening elements present. Like numbers refer to like elements throughout. Furthermore, "coupled", "connected", "responsive", or variants thereof as used herein may include wirelessly coupled, connected, or responsive. As used herein, the singular forms "a", "an" and "the" are intended to include the plural forms as well, unless the context clearly indicates otherwise. Well-known functions or constructions may not be described in detail for brevity and/or clarity. The term "and/or" includes any and all combinations of one or more of the associated listed items.

It will be understood that although the terms first, second, third, etc. may be used herein to describe various elements/operations, these elements/operations should not be limited by these terms. These terms are only used to distinguish one element/operation from another element/operation. Thus, a first element/operation in some embodiments could be termed a second element/operation in other embodiments without departing from the teachings of present inventive concepts. The same reference numerals or the same reference designators denote the same or similar elements throughout the specification.

As used herein, the terms "comprise", "comprising", "comprises", "include", "including", "includes", "have", "has", "having", or variants thereof are open-ended, and include one or more stated features, integers, elements, steps, components or functions but does not preclude the presence or addition of one or more other features, integers, elements, steps, components, functions or groups thereof. Furthermore, as used herein, the common abbreviation "e.g.", which derives from the Latin phrase "exempli gratia," may be used to introduce or specify a general example or examples of a previously mentioned item, and is not intended to be limiting of such item. The common abbreviation "i.e.", which derives from the Latin phrase "id est," may be used to specify a particular item from a more general recitation.

Example embodiments are described herein with reference to block diagrams and/or flowchart illustrations of computer-implemented methods, apparatus (systems and/or devices) and/or computer program products. It is understood that a block of the block diagrams and/or flowchart illustrations, and combinations of blocks in the block diagrams and/or flowchart illustrations, can be implemented by computer program instructions that are performed by one or more computer circuits. These computer program instructions may be provided to a processor circuit of a general purpose computer circuit, special purpose computer circuit, and/or other programmable data processing circuit to produce a machine, such that the instructions, which execute via the processor of the computer and/or other programmable data processing apparatus, transform and control transistors, values stored in memory locations, and other hardware components within such circuitry to implement the functions/acts specified in the block diagrams and/or flowchart block or blocks, and thereby create means (functionality) and/or structure for implementing the functions/acts specified in the block diagrams and/or flowchart block(s).

These computer program instructions may also be stored in a tangible computer-readable medium that can direct a computer or other programmable data processing apparatus to function in a particular manner, such that the instructions stored in the computer-readable medium produce an article of manufacture including instructions which implement the functions/acts specified in the block diagrams and/or flowchart block or blocks. Accordingly, embodiments of present inventive concepts may be embodied in hardware and/or in software (including firmware, resident software, microcode, etc.) that runs on a processor such as a digital signal processor, which may collectively be referred to as "circuitry," "a module" or variants thereof.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated. Finally, other blocks may be added/inserted between the blocks that are illustrated, and/or blocks/operations may be omitted without departing from the scope of inventive concepts. Moreover, although some of the diagrams include arrows on communication paths to show a primary direction of communication, it is to be understood that communication may occur in the opposite direction to the depicted arrows.

Many variations and modifications can be made to the embodiments without substantially departing from the principles of the present inventive concepts. All such variations and modifications are intended to be included herein within the scope of present inventive concepts. Accordingly, the above disclosed subject matter is to be considered illustrative, and not restrictive, and the appended examples of embodiments are intended to cover all such modifications, enhancements, and other embodiments, which fall within the spirit and scope of present inventive concepts. Thus, to the maximum extent allowed by law, the scope of present inventive concepts are to be determined by the broadest permissible interpretation of the present disclosure including the following examples of embodiments and their equivalents, and shall not be restricted or limited by the foregoing detailed description.

What is claimed is:

1. An implantable osteodistraction device comprising:
an outer tube;
an inner tube disposed at least partially within the outer tube;
an inductive power transfer circuit connected to and at least partially within one of the outer and inner tubes, and configured to receive power through inductive coupling to an external power coil;
a shape-memory-alloy actuator connected to and at least partially within the one of the outer and inner tubes, the shape-memory-alloy actuator including a shape-memory-alloy element electrically connected to be powered by the inductive power transfer circuit, the shape-memory-alloy element configured to transition from a first phase to a second phase with a corresponding change in shape responsive to threshold resistive heating; and
a force transmission apparatus including a one-way linear movement locking clutch connected to the shape-memory-alloy actuator and slidably connected to another one of the outer and inner tubes, the one-way linear movement locking clutch configured to convert change in shape of the shape-memory-alloy element, by transition from one of the first and second phases to the other one of the first and second phases, to an extension of the inner tube from within the outer tube and to prevent contraction of the inner tube into the outer tube when the shape-memory-alloy element transitions from the other one of the first and second phases to the one of the first and second phases
wherein the one-way linear movement locking clutch of the force transmission apparatus comprises:
at least one ring apparatus including an angle ring and a roller, at least one portion of the angle ring having a slanted surface relative to and facing an inner surface of the other one of the outer and inner tubes, the roller being positioned between the slanted surface and the inner surface of the other one of the outer and inner tubes,
wherein when the shape-memory-alloy element transitions from the other one of the first and second phases to the one of the first and second phases which urges contraction of the inner tube into the outer tube, friction rolls the roller on the slanted surface to become wedged between the slanted surface and the inner surface of the other one of the outer and inner tubes and prevent contraction of the inner tube into the outer tube,
wherein the one-way linear movement locking clutch comprises:
a plurality of the ring apparatuses; and
a rod extending through a center opening of the angle rings of the plurality of ring apparatuses to arrange the angle rings along a major axis of the one of the outer and inner tubes, the rod attached to the shape-memory-alloy actuator.

2. The implantable osteodistraction device of claim 1, wherein the one-way linear movement locking clutch is configured to convert change in shape of the shape-memory-alloy element, by transition from the first phase to the second phase, to an extension of the inner tube from within the outer tube and to prevent contraction of the inner tube into the outer tube when the shape-memory-alloy element transitions from the second phase to the first phase.

3. The implantable osteodistraction device of claim 1, wherein the shape-memory-alloy actuator further comprises:
a priestess spring coupled between the shape-memory-alloy element and the force transmission apparatus, and configured to apply tensile force to the shape-memory-alloy element to promote extension of the shape-memory-alloy element when transitioning from the other one of the first and second phases to the one of the first and second phases.

4. The implantable osteodistraction device of claim 1, wherein the ring apparatus comprises a plurality of surface recesses in the angle ring that are spaced apart circumferentially around the angle ring and have the slanted surface, and a plurality of rollers positioned in different ones of the surface recesses.

5. The implantable osteodistraction device of claim 1, wherein the roller comprises:
one of a spherical ball and a cylinder.

6. The implantable osteodistraction device of claim 1, wherein the one-way linear movement locking clutch of the force transmission apparatus comprises:
a first rod connected to the shape-memory-alloy actuator; and
at least one ring apparatus including an angle ring and a roller, the angle ring encircling a second rod and a portion of the angle ring having a slanted surface facing the rod, the roller being positioned between the slanted surface and the rod,
wherein when the shape-memory-alloy element transitions from the other one of the first and second phases to the one of the first and second phases, which causes the locking clutch to couple to the first rod causing movement and the lengthening of the implantable osteodistraction device.

7. The implantable osteodistraction device of claim 1, wherein the shape-memory-alloy actuator comprises:
a plurality of rod-shaped shape-memory-alloy elements extending between a first member and a spaced apart second member, the first member connected to and at least partially within the one of the outer and inner tubes, the second member connected to the one-way linear movement locking clutch of the force transmission apparatus.

8. The implantable osteodistraction device of claim 7, wherein the rod-shaped shape-memory-alloy elements comprise an alloy of nickel and titanium.

9. The implantable osteodistraction device of claim 7, wherein the shape-memory-alloy actuator comprises:
a plurality of elastic rods extending between the first and second members.

10. The implantable osteodistraction device of claim 9, wherein the elastic rods are arranged interspersed with the rod-shaped shape-memory-alloy elements.

11. The implantable osteodistraction device of claim 9, wherein:
the elastic rods comprise a metal and the rod-shaped shape-memory-alloy elements comprise a Nitinol alloy of nickel and titanium; and
the first and second members comprise clamping plates having openings configured to receive and fixedly clamp to opposite ends of the elastic rods and the rod-shaped shape-memory-alloy elements.

12. The implantable osteodistraction device of claim 7, wherein the shape-memory-alloy actuator further comprises:
a prestress spring configured to apply tensile force to the rod-shaped shape-memory-alloy elements to promote extension of the rod-shaped shape-memory-alloy elements when transitioning from the second phase to the first phase.

13. An osteodistraction system comprising:
an inductive power unit comprising at least one processor and a power supply configured to be controlled by the at least one processor to provide a controlled current level to an inductive power coil; and
an implantable osteodistraction device including:
an outer tube,
an inner tube disposed at least partially within the outer tube,
an inductive power transfer circuit connected to and at least partially within one of the outer and inner tubes, and configured to receive power through inductive coupling to the inductive power coil of the inductive power unit,
a shape-memory-alloy actuator connected to and at least partially within the one of the outer and inner tubes, the shape-memory-alloy actuator including a shape-memory-alloy element electrically connected to be powered by the inductive power transfer circuit, the shape-memory-alloy element configured to transition from a first phase to a second phase with a corresponding change in shape responsive to threshold resistive heating, and
a force transmission apparatus including a one-way linear movement locking clutch connected to the shape-memory-alloy actuator and slidably connected to another one of the outer and inner tubes, the one-way linear movement locking clutch configured to convert change in shape of the shape-memory-alloy element, by transition from one of the first and second phases to the other one of the first and second phases, to an extension of the inner tube from within the outer tube and to prevent contraction of the inner tube into the outer tube when the shape-memory-alloy element transitions from the other one of the first and second phases to the one of the first and second phases
wherein the at least one processor is configured to control the power supply to provide the controlled current level to the inductive power coil for a first defined time duration sufficient to transition the shape-memory-alloy element from the first phase to the second phase with the corresponding change in shape, and to thereafter prevent the power supply from providing the controlled current level to the inductive power coil for at least a second defined time duration sufficient to transition the shape-memory-alloy element from the second phase to the first phase with a corresponding reversal in the change in shape.

14. The osteodistraction system of claim 13, further comprising:
a network interface configured to communicate through a communication network,
wherein the at least one processor is configured to generate a patient treatment diary tracking time of day for each occurrence of the power supply being controlled to transition the shape-memory-alloy element from the first phase to the second phase with the corresponding change in shape, and to communicate the patient treatment diary through the network interface.

15. The osteodistraction system of claim 13, further comprising:
a network interface configured to be communicate through a communication network,
wherein the at least one processor is configured to receive a prescribed activation schedule through the network interface and to control the power supply to provide the controlled current level to the inductive power coil according to the prescribed activation schedule.

* * * * *